United States Patent
Forshag et al.

(10) Patent No.: US 9,421,248 B2
(45) Date of Patent: Aug. 23, 2016

(54) ALPHA 1-PROTEINASE INHIBITOR FOR DELAYING THE ONSET OR PROGRESSION OF PULMONARY EXACERBATIONS

(71) Applicant: GRIFOLS, S.A., Barcelona (ES)

(72) Inventors: Mark Forshag, Carrboro, NC (US); Royce Waltrip, Chapel Hill, NC (US); Les Garlinghouse, Cary, NC (US); William Barnett, Chapel Hill, NC (US)

(73) Assignee: GRIFOLS, S.A., Barcelona (ES)

( * ) Notice: Subject to any disclaimer, the term of this patent is extended or adjusted under 35 U.S.C. 154(b) by 0 days.

(21) Appl. No.: 14/369,662

(22) PCT Filed: Nov. 22, 2012

(86) PCT No.: PCT/IB2012/056616
§ 371 (c)(1),
(2) Date: Jun. 27, 2014

(87) PCT Pub. No.: WO2013/098672
PCT Pub. Date: Jul. 4, 2013

(65) Prior Publication Data
US 2015/0011460 A1 Jan. 8, 2015

Related U.S. Application Data

(60) Provisional application No. 61/581,708, filed on Dec. 30, 2011.

(51) Int. Cl.
*A61K 38/57* (2006.01)
*A61K 38/00* (2006.01)
*A61M 15/00* (2006.01)
*A61K 45/06* (2006.01)
*A61M 16/14* (2006.01)

(52) U.S. Cl.
CPC .............. *A61K 38/57* (2013.01); *A61K 38/00* (2013.01); *A61K 45/06* (2013.01); *A61M 15/0018* (2014.02); *A61M 15/0085* (2013.01); *A61M 16/14* (2013.01)

(58) Field of Classification Search
CPC ....... A61K 38/57; A61K 38/55; C07K 14/811
See application file for complete search history.

(56) References Cited

U.S. PATENT DOCUMENTS

2009/0131305 A1 5/2009 Bauer

FOREIGN PATENT DOCUMENTS

| WO | 2005/048985 A2 | 6/2005 |
| WO | 2010/009388 A1 | 1/2010 |
| WO | WO 2010009388 A1 * | 1/2010 |
| WO | 2011/056793 A2 | 5/2011 |

OTHER PUBLICATIONS

Kropp et al., "Inhalation of [123I]a1—Protease Inhibitor: Toward a New Therapeutic Concept of a1—Protease Inhibitor Deficiency?", J Nucl Med 2001; 42:744-751.*
Cantin et al., "Prolastin aerosol therapy and sputum taurine in cystic fibrosis", Clinical and Investigative Medicine, 2006, p. 201-207.*
McDowell et al., "Anthropometric Reference Data for Children and Adults: United States, 2003-2006", U.S. Department of Health and Human Services, 2008, pp. 1-44 and 48.*
Karnaukhova et al., "Recombinant human alpha-1 proteinase inhibitor: towards therapeutic use", Amino Acid, 2006, pp. 317-323.*
Goss et al., "Exacerbations in cystic fibrosis 1: Epidemiology and pathogenesis", Thorax, 2007, pp. 360-367.*
International Search Report and Written Opinion dated Jul. 18, 2013 for PCT/IB2012/056616.

* cited by examiner

*Primary Examiner* — Lianko Garyu
(74) *Attorney, Agent, or Firm* — Knobbe, Martens, Olson & Bear, LLP

(57) ABSTRACT

An $alpha_1$-proteinase inhibitor delays the onset or progression of pulmonary exacerbations. In addition, methods delay the onset or diminish the progression of pulmonary exacerbations by the administration of inhaled $alpha_1$-proteinase inhibitor.

15 Claims, 3 Drawing Sheets

FIG. 1

MPSSVSWGILLLAGLCCLVPVSLA EDPQGDAAQKTDTSHHDQDHPTFNKITPNL
AEFAFSLYRQLAHQSNSTNIFFSPVSIATAFAMLSLGTKADTHDEILEGLNFNLT
EIPEAQIHEGFQELLRTLNQPDSQLQLTTGNGLFLSEGLKLVDKFLEDVKKLYHS
EAFTVNFGDTEEAKKQINDYVEKGTQGKIVDLVKELDRDTVFALVNYIFFKGKWE
RPFEVKDTEEEDFHVDQVTTVKVPMMKRLGMFNIQHCKKLSSWVLLMKYLGNATA
IFFLPDEGKLQHLENELTHDIITKFLENEDRRSASLHLPKLSITGTYDLKSVLGQ
LGITKVFSNGADLSGVTEEAPLKLSKAVHKAVLTIDEKGTEAAGAMFLEAIPMSI
PPEVKFNKPFVFLMIEQNTKSPLFMGKVVNPTQK 1-24 signal peptide
E25-K418 mature peptide
N70 glycosylation
N107 glycosylation
N271 glycosylation
C256 S-nitrosylation
G368-K392 reactive center loop
F376 proteolytic cleavage site
M382-S383 reactive bond Flow Diagram of a Method for Preparing A1PI

ALPHA 1-PROTEINASE INHIBITOR FOR DELAYING THE ONSET OR PROGRESSION OF PULMONARY EXACERBATIONS

CROSS REFERENCE TO RELATED APPLICATIONS

This application is the U.S. National Phase of International Application No. PCT/IB2012/056616, filed Nov. 22, 2012, designating the U.S. and published as WO 2013/098672 on Jul. 4, 2013 which claims the benefit of U.S. Provisional Patent Application No. 61/581,708, filed Dec. 30, 2011.

REFERENCE TO SEQUENCE LISTING

The present application incorporates by reference the sequence listing submitted as an ASCII text filed via EFS-Web. The Sequence Listing is provided as a file entitled Seq_List_DURC6.txt, created on Jun. 26, 2014, which is approximately 4.4 Kb in size.

TECHNICAL FIELD

Described herein are methods of delaying onset or diminishing the progression of pulmonary exacerbations by the administration of inhaled alpha$_1$-proteinase inhibitor.

BACKGROUND

Alpha$_1$-proteinase inhibitor (abbreviated herein as A1PI; also known as alpha-1 protease inhibitor, alpha-1 PI, A$_1$PI, α-1 PI, α$_2$PI, alpha-1 trypsin inhibitor, alpha-1 antitrypsin, alpha1AT, A1A, and A1AT, AAT, inter alia), is the major serine protease inhibitor (serpin) in humans. A1PI is expressed as a 418 amino acid protein with residues 1-24 being a signal peptide. The mature protein, consisting of residues 25-418, is a single chain glycoprotein having a molecular weight of about 51 kD. See FIG. 1. While A1PI does not contain any disulfide bonds, the protein is highly structured, with 80% of the amino acids residing in eight well-defined α-helices or three large β-sheets. Three asparagine-linked carbohydrates are found on Asn 70, Asn 107, and Asn 271 (numbered as in the full-length protein). This gives rise to multiple A1PI isoforms, having isoelectric points in the range of 4.0 to 5.0. The glycan monosaccharides include N-acetylglucosamine, mannose, galactose, fucose, and sialic acid.

Normal plasma concentrations of A1PI range from 1.3 to 3.5 mg/mL. A1PI functions by protecting cells from proteases involved in clotting and inflammation. A1PI inhibits trypsin, chymotrypsin, and various forms of elastases, skin collagenase, renin, urokinase, and proteases of polymorphonuclear lymphocytes, among others. A1PI serves as a pseudo-substrate for these proteases, which attack the reactive center loop of the A1PI molecule (residues Gly 368-Lys 392) by cleaving the bond between Met 358-Ser 359 residues forming an A1PI-protease complex. This complex is rapidly removed from the blood circulation.

One of the endogenous roles of A1PI is to regulate the activity of neutrophil elastase, which breaks down foreign proteins and injures native tissue present in the lung. In the absence of sufficient quantities of A1PI, the elastase breaks down lung tissue, which over time results in chronic lung tissue damage and emphysema.

The A1PI protein is an acute phase reactant protein and, as such, its synthesis is amplified during episodes of inflammation or stress, which particularly occurs in exacerbation periods. A1PI deficient patients risk severe lung damage during exacerbation periods, due to the inability to mount an effective acute phase A1PI elevation. Relative deficiencies of A1PI may also occur in normal individuals during acute exacerbation periods, resulting in the excess of neutrophil elastase, which leads to the destruction of lung tissue.

Intravenous A1PI has been use as a treatment for alpha$_1$-antitrypsin deficiency (AATD; i.e., A1PI deficiency), a congenital disease. The consequence of the low levels of A1PI in the lower respiratory tract epithelial lining fluid of individuals with AATD is an insufficient antineutrophil elastase protective screen of the lung, such that a neutrophil elastase is able to act unimpeded to attack and destroy alveolar structures. The resulting lung damage is greatly accelerated by cigarette smoking and is irreversible.

In addition, inhaled A1PI has been proposed as an acute therapy to shorten the severity and duration of established acute pulmonary exacerbations. See U.S. Pat. Nos. 7,879,800 and 7,973,005. However, established pulmonary exacerbations can be difficult to eradicate using A1PI. In addition, repetitive exacerbations damage lung tissue and can progressively reduce a subject's FEV$_1$. The administration of A1PI at the initiation of inflammation is believed to be more efficacious than waiting for additional exacerbation symptoms to develop, which can lag behind the onset of inflammation by hours to days. Improved therapy that delays the onset or diminishes the progression of pulmonary exacerbations a priori is desirable.

SUMMARY

Described herein are methods for delaying the onset or diminishing the progression of pulmonary exacerbations in a subject in need thereof comprising administering to the subject an effective amount of A1PI via inhalation.

In one aspect of the method described herein, the A1PI is aerosolized.

In another aspect of the method described herein, the A1PI is administered using a nebulizer.

In another aspect of the method described herein, the A1PI is administered at least once per day.

In another aspect of the method described herein, the effective amount of A1PI is about 25 mg to about 750 mg A1PI per day.

In another aspect of the method described herein, the effective amount of A1PI is about 0.5 mg/kg/day to about 15 mg/kg/day.

In another aspect of the method described herein, the subject in need thereof is at least 12 years old.

In particular embodiments of the method described herein, the pulmonary exacerbations are associated with cystic fibrosis, COPD, AATD, emphysema, asthma, mycobacterial infection, pneumonia, bronchiectasis, or chronic bronchitis.

In particular embodiments of the method described herein, the pulmonary exacerbations are associated with increased severity of exacerbations; increased frequency of exacerbations; decreased lung function; decreased FEV$_1$; increased pulmonary tissue loss; decreased alpha$_1$-proteinase inhibitor levels; increased pulmonary elastase levels; increased pulmonary infections; increased pulmonary bacterial load; or increased cardiac dysrhythmia.

In another aspect of the method described herein, the A1PI is purified by the method described in U.S. Patent Application Publication No. US 2011/0237781 A1.

In another aspect of the method described herein, the A1PI is recombinant A1PI.

In another aspect of the method described herein, the A1PI is purified by a method for purifying A1PI from an aqueous solution containing A1PI, the method comprising: (a) removing a portion of contaminating proteins from the aqueous solution by precipitation in order to obtain a purified solution containing A1PI; (b) passing the purified solution through an anion exchange resin so that A1PI binds to the anion exchange resin; (c) eluting A1PI from the anion exchange resin to obtain an eluted solution containing A1PI; (d) passing the eluted solution through a cation exchange resin; (e) collecting a flow-through from the cation exchange resin that contains A1PI; and (f) contacting the eluted solution of step (c) or the flow-through of step (e) with a hydrophobic adsorbent of at least one HIC medium.

Also described herein is method of delaying onset or progression of one or more symptoms associated with a pulmonary disorder or disease in a subject in need thereof comprising daily administration of an effective amount of A1PI by inhalation; wherein the A1PI is aerosolized; wherein the A1PI is administered using a nebulizer; wherein the effective amount of A1PI is about 25 mg to about 750 mg A1PI per day; wherein the effective amount of A1PI is about 0.5 mg/kg/day to about 15 mg/kg/day; wherein the subject is at least 12 years old; wherein the pulmonary disorder or disease is cystic fibrosis; COPD; AATD; emphysema; asthma; mycobacterial infection; pneumonia; bronchiectasis; or chronic bronchitis; and wherein the pulmonary disorder or disease is associated with one or more of pulmonary exacerbations; increased severity of exacerbations; increased frequency of exacerbations; decreased duration between exacerbations; decreased lung function; decreased $FEV_1$; increased pulmonary tissue loss; decreased A1PI levels; increased pulmonary elastase levels; increased pulmonary infections; increased pulmonary bacterial load; or increased cardiac dysrhythmia.

Also described herein is a method for identifying a subject in need of A1PI maintenance therapy for delaying the onset or diminishing the progression of pulmonary exacerbations comprising evaluating one or more of the prospective subject's (a) age; (b) history of exacerbations; (c) lung function ($FEV_1$); (d) chronic productive cough (mucus producing); (e) upper and lower airways' infectious pathogen burden; (f) expiratory gas markers of respiratory inflammation; (g) response to exogenous challenge testing for airways hyperresponsiveness; (h) number and classes of concomitant medications; (i) genetic risk profile for respiratory disease; and (j) environmental variables such as smoking history, allergies, occupational risk factors and/or exposure to air pollution; and wherein a determination is made that the subject is (or is not) a candidate for A1PI maintenance therapy based on the aforesaid criteria.

Also described herein are methods for identifying subjects with elevated risk for pulmonary exacerbations suitable for A1PI maintenance therapy, the method comprising evaluating one or more of the prospective subject's (a) age; (b) history of exacerbations; (c) lung function ($FEV_1$); (d) chronic productive cough (mucus producing); (e) upper and lower airways' infectious pathogen burden; (f) expiratory gas markers of respiratory inflammation; (g) response to exogenous challenge testing for airways hyperresponsiveness; (h) number and classes of concomitant medications; (i) genetic risk profile for respiratory disease; and (j) environmental variables such as smoking history, allergies, occupational risk factors and/or exposure to air pollution; and wherein a determination is made that the subject is (or is not) a candidate for A1PI maintenance therapy based on the aforesaid criteria.

Also described herein is the use of A1PI for delaying onset or progression of pulmonary exacerbations in a subject in need thereof comprising the daily administration of an effective amount of inhaled A1PI.

Also described herein is the use of A1PI for delaying onset or progression of pulmonary disease in a subject in need thereof comprising the daily administration of an effective amount of inhaled A1PI.

Also described herein is the use of A1PI for maintenance of a pulmonary disease-free state comprising the daily administration of an effective amount of inhaled A1PI.

Also described herein is an apparatus for administering aerosolized A1PI for inhalation comprising a nebulizer.

In one aspect of the apparatus for administering aerosolized A1PI for inhalation comprising a nebulizer, the nebulizer comprises (a) an aerosol generator comprising: a liquid storage container comprising the liquid pharmaceutical composition; a diaphragm having a first side and an opposite second side, the diaphragm having a plurality of openings extending therethrough from the first side to the second side, where the first side is connected to the liquid storage container such that the liquid filled into the liquid storage container comes into contact with the first side of the diaphragm; and a vibration generator capable of vibrating the diaphragm so that the liquid filled into the liquid storage container is atomized on the second side of the diaphragm through the openings of the diaphragm; (b) a mixing chamber into which the aerosol generator expels said aerosol, the mixing chamber in contact with the second side of the diaphragm; and (c) an inhalation valve that is open to allow an inflow of ambient air into the mixing chamber during an inhalation phase and is closed to prevent escape of said aerosol from the mixing chamber during an exhalation phase; wherein an A1PI pharmaceutical composition is nebulized by the inhalation nebulizer to form an aerosol composition.

In another aspect of the apparatus for administering aerosolized A1PI for inhalation described herein, the apparatus can include an exhalation valve.

Also described herein is a means for administering aerosolized A1PI for inhalation comprising a nebulizer.

Also described herein is a method of delaying onset or diminishing the progression of one or more symptoms associated with pulmonary exacerbations in a subject comprising a method for identifying subjects with elevated risk for pulmonary exacerbations suitable for A1PI maintenance therapy, the method comprising evaluating one or more of the prospective subject's (a) age; (b) history of exacerbations; (c) lung function ($FEV_1$); (d) chronic productive cough (mucus producing); (e) upper and lower airways' infectious pathogen burden; (f) expiratory gas markers of respiratory inflammation; (g) response to exogenous challenge testing for airways hyperresponsiveness; (h) number and classes of concomitant medications; (i) genetic risk profile for respiratory disease; and (j) environmental variables such as smoking history, allergies, occupational risk factors and/or exposure to air pollution; and wherein a determination is made that the subject is (or is not) a candidate for A1PI maintenance therapy based on the aforesaid criteria; and administering to the subject an effective amount of A1PI via inhalation.

Also described herein is a method for delaying onset or diminishing progression of one or more symptoms associated with a pulmonary exacerbation in a subject, the method comprising the daily administration of an effective amount of A1PI by inhalation, wherein the subject has one or more of (a) an elevated risk for acute pulmonary exacerbation; (b) a significant decline of respiratory function; or (c) a history of pulmonary exacerbations associated with cystic fibrosis, COPD, AATD, emphysema, asthma, mycobacterial infection, pneumonia, bronchiectasis, or chronic bronchitis; wherein the subject receives inhaled A1PI administered via aerosol generated by a nebulizer one or more times per day; and wherein the cumulative effective dose of A1PI is from about 25 mg to about 750 mg per day.

Another aspect described herein is a method for delaying onset or diminishing progression of one or more symptoms associated with a pulmonary exacerbation in a subject, the method comprising the daily administration of an effective amount of A1PI by inhalation, wherein the method can result in reduced hospitalization; reduced intensive care or mechanical ventilation need; reduced healthcare utilization or burden; reduced absences from school or work; decreased antibiotic need; decreased steroid need; decreased relapse frequency; decreased morbidity; and improved quality of life for subjects.

Other embodiments described herein are kits for delaying onset or diminishing progression of one or more symptoms associated with a pulmonary exacerbation in a subject.

One aspect described herein is a kit for delaying the onset or progression of pulmonary exacerbations comprising A1PI in a ready to use container.

Another aspect described herein is a kit, further comprising at least one dose of at least one composition for use in the methods described herein. In certain aspects, for example, the kit comprises at least one daily dose or one effective dose of A1PI.

Another aspect described herein is a kit, further comprising at least one dose of at least one composition for delaying the onset or progression of pulmonary exacerbations as described herein and a device for delivery of the composition.

Another aspect described herein is a kit, further comprising one or more additional agents, as described herein, for delaying the onset or progression of pulmonary exacerbations, including one or more bronchodilator, one or more corticosteroid, and/or one or more mucolytics, one or more expectorants, one or more antibiotics or one or more antioxidants.

Another aspect described herein is a kit for delaying onset or progression of pulmonary exacerbations in a subject in need thereof, as described herein, comprising: at least one dose of A1PI, or at least one effective dose of A1PI, each contained in individual containers; instructions for using the kit and evaluating a subject in need thereof; optionally, an apparatus for administering A1PI by inhalation; optionally, one or more additional agents, as described herein, for delaying the onset or progression of pulmonary exacerbations, including one or more bronchodilators, one or more corticosteroids, and/or one or more mucolytics, one or more expectorants, one or more antibiotics or one or more antioxidants.

BRIEF DESCRIPTION OF THE DRAWINGS

FIG. 1: The primary sequence of full-length human alpha$_1$-proteinase inhibitor, A1PI (SEQ ID NO:1). The mature protein consists of amino acids 25-419.

DETAILED DESCRIPTION

Figure 2:
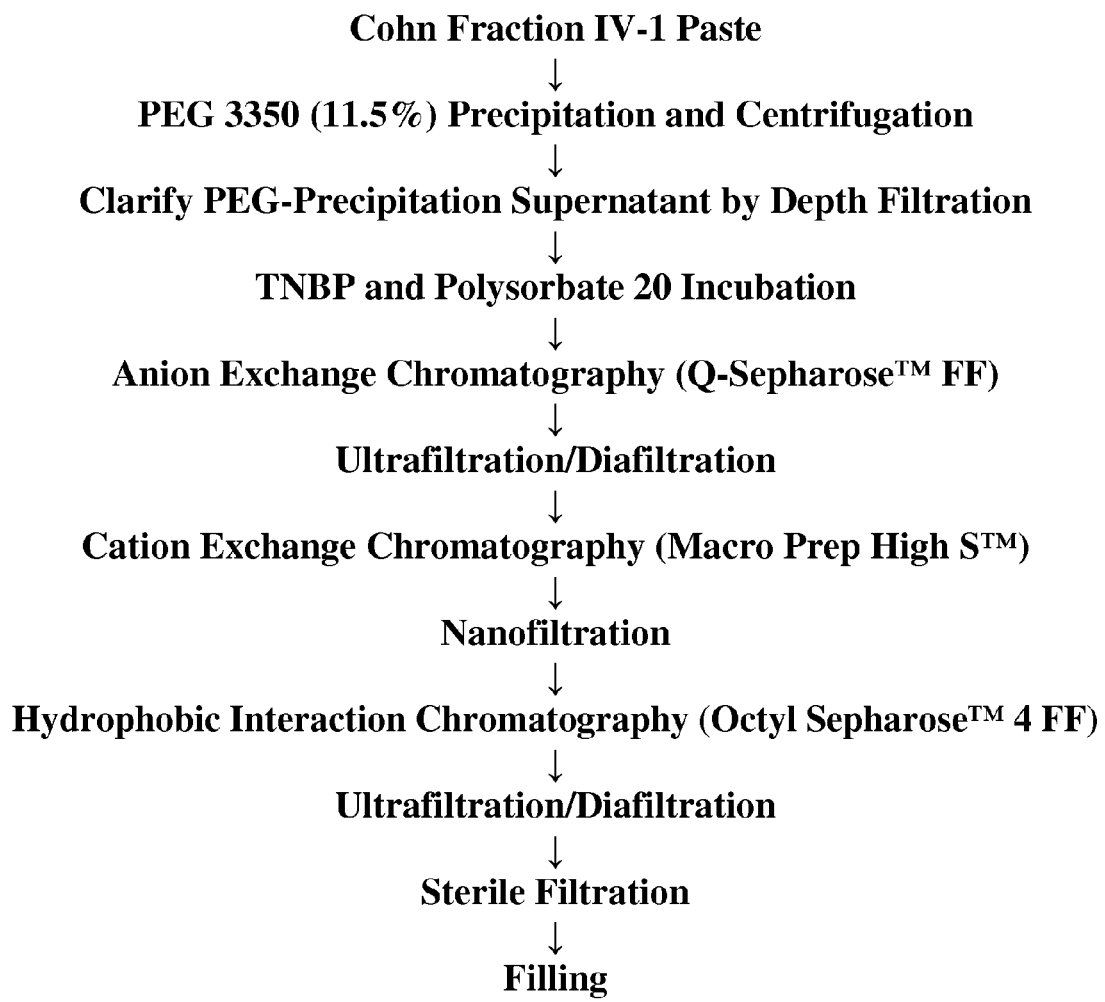
FIG. 2: Flow diagram of the purification scheme for human A1PI-HC from Cohn fraction IV-1 paste. See U.S. Patent Application Publication No. US 2011/0237781 A1.

A1PI has not heretofore been used as chronic (long-term) maintenance therapy by the respiratory route for delaying onset or diminishing the progression of pulmonary exacerbations.

As used herein, the terms and phrases "exacerbation," "pulmonary exacerbation," "exacerbation period," and "exacerbation episode" are used interchangeably to describe an increase in the severity of a pulmonary disease or disorder and any of its symptoms, which are associated with a worsening of quality of life. Exacerbations are frequent in patients with chronic lung diseases in general. "Pulmonary exacerbations" refer to the worsening and/or increase in severity and/or magnitude of a pulmonary disease symptom due to an inflammation or infection. A pulmonary exacerbation is generally characterized by: (a) shortness of breath; (b) fatigue; (c) increased cough; (d) a chronic, more productive cough (i.e., increased mucus expectoration); (e) a reduction in forced expiratory volume ($FEV_1$); (f) expiratory gas markers of respiratory inflammation; and (g) a genetic risk profile for respiratory disease, or other markers of pulmonary function. Pulmonary exacerbations are highly correlated with long-term deterioration of lung tissue and function.

"Acute" as used herein means arising suddenly and manifesting intense severity. With relation to delivery or exposure, "acute" refers to a relatively short duration.

"Chronic" as used herein means lasting a long time, sometimes also meaning having a low intensity. With regard to delivery or exposure, "chronic" means for a prolonged period or long-term.

As used herein, the phrase "cystic fibrosis" or "CF" refer to an inherited autosomal recessive disorder caused by mutations in the gene encoding the cystic fibrosis transmembrane conductance regulator (CFTR) chloride channel.

"Alpha$_1$-antitrypsin deficiency" or "AATD," as used herein, refers to an autosomal recessive genetic disorder causing both lung and liver diseases. AATD affects 1 in 1,800 live births in Northern European and North American populations. The fundamental pathological process of AATD is the accumulation of mutant alpha$_1$-protease inhibitor molecules as polymers within hepatocytes. The resultant low levels of A1PI in the serum result in lung damage by proteinases, and eventually emphysema. The lung disease in AATD patients is usually of an earlier onset than in patients with chronic obstructive pulmonary disease (COPD) and often appears to be out of proportion to their smoking history. The typical pattern shows lower lobe predominant or pan-lobular emphysema. The pathogenesis of emphysema associated with AATD is closely related to neutrophil elastase. Leucocyte elastase, a neutrophil enzyme, binds to the active site of A1PI and permanently inactivates it in a stiochastic manner. High levels of elastase cause elastin degradation, resulting in significant lung tissue injury. Smoking is a definite compounding factor for the development of lung disease. Genetic factors and environmental risk factors, such as smoking history, allergies, occupational exposure to pulmonary irritants, and/or exposure to air pollution, are also implicated in the pathogenesis of A1PI-associated lung diseases.

The term "emphysema," as is used herein, refers to a pathological condition of the lungs in which there is a decrease in respiratory function and often breathlessness due to an abnormal increase in the size of the air spaces, caused by irreversible expansion of the alveoli and/or by the destruction of alveolar walls by neutrophil elastase. Emphysema is a pathological condition of the lungs marked by an abnormal increase in the size of the air spaces, resulting in strenuous breathing and an increased susceptibility to infection. It can be caused by irreversible expansion of the alveoli or by the destruction of alveolar walls. Due to the damage caused to lung tissue, elasticity of the tissue is lost, leading to trapped air in the air sacs and to impairment in the exchange of oxygen and carbon dioxide. In light of the walls breakdown, the airway support is lost, leading to obstruction in the airflow. Emphysema and chronic bronchitis frequently co-exist together to comprise chronic obstructive pulmonary disease.

As used herein, the phrase "chronic obstructive pulmonary disease" or "COPD," refers to a disease state characterized by airflow limitation that is not fully reversible. The airflow limitation is usually both progressive and associated with an abnormal inflammatory response of the lungs to noxious particles or gases. Symptoms, functional abnormalities, and complications of COPD can be attributed to this underlying phenomenon of abnormal inflammatory response and to processes related thereto.

The chronic airflow limitations characteristic of COPD is caused by a mixture of small airway disease (obstructive bronchiolitis) and parenchymal destruction (emphysema), the relative contribution of each vary from person to person. Chronic inflammation causes remodeling and narrowing of the small airway. Destruction of the lung parenchyma, also by inflammation processes, leads to the loss of alveolar attachments to the small airways and decrease the lung elastic recoil; these changes diminish the ability of the airways to remain open during expiration.

In addition to inflammation, two other processes are thought to be important in the pathogenesis of COPD: the imbalance of proteinases and antiproteinases in the lung, and oxidative stress. These processes may themselves be consequences of inflammation, or they may arise from environmental (e.g., oxidant compounds in cigarette smoke) or genetic (e.g., alpha$_1$-antitrypsin deficiency) factors.

The progressive course of COPD is complicated by exacerbation episodes that have many causes and occur with increasing frequency as the disease progresses. The most common causes for an exacerbation are infection of the tracheobronchial tree and air-pollution, but the cause of about one third of monitored severe exacerbations cannot be identified. The effect of exacerbations may be more apparent in patients with mild to moderate disease and an increased number of exacerbations were shown to correlate with the decline in gas transfer during expiration. Exacerbations can be treated at home, but very often require medical intervention and hospitalization. Hospital mortality of patients admitted for an exacerbation of COPD is approximately 10%, and the long-term survival is poor.

A three-year observational study of 2138 COPD patients by Hurst et al. showed that an apparent exacerbation-prone phenotype exists. Hurst et al., *N. Engl. J. Med.* 363: 1128-1138. This cohort of patients had two or more exacerbations per year. The best predictor of the exacerbation-prone phenotype is a history of frequent exacerbations. Hurst et al., *N. Engl. J. Med.* 363: 1128-1138.

"Asthma," as used herein, refers to a chronic respiratory disease, often arising from allergies, that is characterized by sudden recurring attacks of labored breathing, chest constriction, and coughing. In a typical asthmatic reaction, IgE antibodies predominantly attach to mast cells that lie in the lung interstitium in close association with the bronchioles and small bronchi. An antigen entering the airway will thus react with the mast cell-antibody complex, causing release of several substances, including, but not limited to interleukin cytokines, chemokines, and arachidonic acid-derived mediators, resulting in bronchoconstriction, airway hyperreactivity, excessive mucus secretion, and airway inflammation.

"Pneumonia," as used herein, refers to an acute infection of one or more functional elements of the lung, including alveolar spaces and interstitial tissue. Generally, pneumonia can result from acute lung disease, lung inflammatory disease, or any perturbations in lung function due to factors such as inflammation or coagulation.

"Severe chronic bronchitis" or "bronchiectasis," as used herein, refers to the abnormal and irreversible dilation of the proximal medium-sized bronchi (>2 mm in diameter) caused by destruction of the muscular and elastic components of the bronchial walls. It can be congenital or acquired. Bronchiectasis can be caused by the bacteria *Streptococcus pneumoniae, Haemophilus influenzae, Staphylococus aureus*, and *Moraxella catarrhalis* and the atypical pneumonias *Legionella pneumonia, Chlamydia pneumoniae*, and *Mycoplasma pneumoniae* including *Pseudomonas aeruginosa*.

"Mycobacterial infection," as used herein, refers to the pulmonary infection caused by various species of *Mycobacterium*. "Tuberculosis" or "TB" is one example of an airborne, chronic *Mycobacterium tuberculosis* infection.

The term "subject," as used herein, refers to any animal, individual, or patient to which the methods described herein are performed. Generally, the subject is human, although as will be appreciated by those in the art, the subject may be an animal. Thus, other animals, including mammals such as rodents (including mice, rats, hamsters and guinea pigs), cats, dogs, rabbits, farm animals including cows, horses, goats, sheep, pigs, etc., and non human primates (including monkeys, chimpanzees, orangutans and gorillas) are included within the definition of subject.

A "subject in need thereof," as used herein, refers to a subject having or at risk of developing a pulmonary exacerbation. A subject in need thereof may have or be at risk of developing respiratory disease or disorder that is associated with pulmonary exacerbations.

The terms "treat," "treating," and "treatment," as used herein, refer to delaying the onset or diminishing the progression of pulmonary exacerbations as described herein.

"Inhalation" refers to a method of administration of a compound that delivers an effective amount of the compound so administered or delivered to the tissues of the lungs or lower respiratory tract by inhalation of the compound by the subject, thereby drawing the compound into the lung. As used herein, "administration" is synonymous with "delivery."

The phrases "pulmonary administration," "respiratory administration," "pulmonary delivery," and "respiratory delivery" are synonymous as used herein and refer to the administration and or delivery of A1PI to a subject by inhalation through the mouth and or nose and into the lungs and lower respiratory tract.

As used herein, the phrases "therapeutically effective amount," "effective amount," or "effective dose" are synonymous and refer to an amount of A1PI that is effective to delay onset of or diminish the progression of pulmonary exacerbations over some period of time in the subject to whom it is administered, as described herein. As used herein, "therapeutic effect," refers to the outcome of or consequences resulting from administering a therapeutically effective amount of A1PI to a subject, which can include delaying the onset or progression of pulmonary exacerbations, as described herein, among other effects.

"Therapy" or "therapeutic," as used herein, refers to the administration of an effective amount of A1PI to delay the onset or diminishing the progression of pulmonary exacerbations.

"Maintenance therapy," as used herein, refers to the regular, periodic administration of A1PI to maintain a sufficient level of A1PI in a subject's lungs or circulatory system to have a therapeutic effect on the subject.

"Augmentation therapy," as used herein, refers to supplementing, replacing, or increasing deficient in vivo quantities or concentrations of a biomolecule, such as A1PI, to have a therapeutic effect on a subject.

One aspect of the method described herein, is A1PI maintenance therapy for respiratory diseases or disorders that are associated with pulmonary exacerbations. In some aspects of the methods described herein, A1PI maintenance therapy comprises augmentation therapy.

Non-limiting examples of symptoms associated with pulmonary exacerbations in a subject include those comprising Fuchs' criteria such as changes in sputum; new or increased hemoptysis; increased cough; increased dyspnea; malaise, fatigue, or lethargy; a fever with body temperature above 38° C.; anorexia or weight loss; sinus pain or tenderness; a change in sinus discharge; a change in physical examination of the chest; decrease in pulmonary function ($FEV_1$) by 10 percent or more from a previously recorded value; or any radiographic changes indicative of pulmonary infection. To meet Fuchs' criteria, any four of the foregoing twelve symptoms are present. See Fuchs et al., *N. Engl. J. Med.* 331: 637-642 (1994).

"Alpha$_1$-protease inhibitor" or "A1PI," as used herein, refers to all naturally occurring polymorphs of A1PI. A1PI also refers to A1PI prepared from plasma and A1PI that can be obtained commercially. A1PI also corresponds to human or a non-human A1PI. In some aspects, A1PI is plasma-derived A1PI. In some aspects, A1PI is prepared from Cohn Fraction IV-1 paste. In other aspects, the A1PI is prepared from an albumin-depleted plasma fraction, a Cohn V precipitate, or a pre-purified A1PI preparation fraction. U.S. Pat. Nos. 4,697,003; 5,610,285; 6,093,804; 6,462,180; 6,525,176; 6,974,792; and 7,879,800 are each herein incorporated by reference for its teaching of methods for purifying A1PI.

"Recombinant A1PI," as used herein, refers to A1PI that is the product of recombinant DNA or transgenic technology. The phrase, "recombinant A1PI," also includes functional fragments of A1PI, chimeric proteins comprising A1PI or functional fragments thereof, fusion proteins or fragments of A1PI, homologues obtained by analogous substitution of one or more amino acids of A1PI, and species homologues. For example, the gene coding for A1PI can be inserted into a mammalian gene encoding a milk whey protein in such a way that the DNA sequence is expressed in the mammary gland as described in, e.g., U.S. Pat. No. 5,322,775, which is herein incorporated by reference for its teaching of a method of producing a proteinaceous compound. "Recombinant A1PI," also refers to A1PI proteins synthesized chemically by methods known in the art such as, e.g., solid-phase peptide synthesis. Amino acid and nucleotide sequences for A1PI and/or production of recombinant A1PI are described by, e.g., U.S. Pat. Nos. 4,711,848; 4,732,973; 4,931,373; 5,079,336; 5,134,119; 5,218,091; 6,072,029; and Wright et al., *Biotechnology* 9: 830 (1991); and Archibald et al., *Proc. Natl. Acad. Sci.* (USA), 87: 5178 (1990), are each herein incorporated by reference for its teaching of A1PI sequences, recombinant A1PI, and/or recombinant expression of A1PI.

The phrase "pharmaceutical composition" as used herein includes preparations containing A1PI as described herein. The pharmaceutical composition should contain a therapeutically effective amount of A1PI, i.e., that amount necessary to delay onset or diminish the progression of pulmonary exacerbations over some period of time in a subject to whom it is administered.

Pharmaceutical compositions of A1PI may be manufactured by processes known in the art, e.g., by means of conventional mixing, dissolving, granulating, grinding, pulverizing, dragee-making, levigating, emulsifying, encapsulating, entrapping, or lyophilizing processes. Pharmaceutical compositions thus may be formulated in conventional manner using one or more acceptable diluents or carriers comprising excipients and auxiliaries, which facilitate processing of the active compounds into preparations, which can be used pharmaceutically. Proper formulation is dependent on the route of administration chosen. According to the description herein, the pharmaceutical compositions are formulated in a form suitable for inhalation.

Pharmaceutical compositions of A1PI are currently available. For example, liquid compositions of A1PI suitable for use in the methods described herein may be prepared by rehydrating (reconstituting) lyophilized preparations of plasma-derived, glycosylated, human A1PI, such as ARALAST™ (Alpha Therapeutic Corp.; distributed by Baxter Healthcare Corp.), ZEMARIA™ (CLS Behring), or PROLASTIN® (Grifols Therapeutics Inc., formerly Talecris Biotherapeutics, Inc.). PROLASTIN® is a preferred non-limiting example of a commercially available A1PI composition in a ready-to-use liquid formulation that is compatible with the methods described herein. Administration of A1PI by the inhalation route is thought be more beneficial than intravenous administration because A1PI directly reaches the lower respiratory tract. The inhalation route also requires lower therapeutic doses of A1PI and thus conserves the supply of human plasma-derived A1PI. This route of administration may be also more effective in neutralizing neutrophil elastase and in correcting the imbalance between proteinases and anti-proteinases in the lung tissues. In addition, administration by inhalation is simpler and less stressful for the subject than the intravenous route and reduces the burden on local health care systems by requiring less clinical support.

In some aspects, however, liquid compositions of A1PI suitable for use in the methods described herein may be prepared by rehydrating (reconstituting) dried compositions comprising recombinant A1PI, typically human A1PI, including unglycosylated human A1PI, such as recombinant A1PI, truncated human A1PI, or A1PI fusion proteins. See WO 2002/050287 for examples of A1PI fusion proteins.

"A1PI purified using hydrophobic interaction chromatography" or "A1PI-HC," as used herein, refers to A1PI purified by the methods described herein and in U.S. Patent Application Publication No. US 2011/0237781 A1, which is herein incorporated by reference for such teachings. A1PI-HC is similar to PROLASTIN® and is another non-limiting example of A1PI useful for the methods described herein.

Formulations of pharmaceutical compositions for administration by the inhalation route are known in the art, as well as inhaler systems and devices. Any of the various means known in the art for administering therapeutically active agents by inhalation (pulmonary delivery) can be used in the methods described herein. Such delivery methods are known in the art. See, e.g., Keller, *Int. J. Pharmaceutics* 186: 81-90 (1999); Everard, *J. Aerosol Med.* 14 (Suppl 1): S-59-S-64 (2001); Togger and Brenner, *Am. J. Nursing* 101: 26-(2001). Commercially available aerosolizers for liquid formulations, including jet nebulizers and ultrasonic nebulizers, are useful in the methods described herein.

In general, for administration by inhalation, the active ingredients can be delivered in the form of an aerosol spray from a pressurized metered dose inhaler with the use of a suitable propellant, e.g., dichlorodifluoromethane, trichlorofluoromethane, dichloro-tetrafluoroethane, or carbon dioxide. The active ingredient in the aerosol spray may be in a powder form administered using a dry powder inhaler, or in aqueous liquid aerosol form using a nebulizer. The charge loaded into an inhalation device is formulated accordingly to contain the proper inhalation dose of A1PI for delivery in a single administration. See generally, Chapter 92 of *Remington's Pharmaceutical Sciences*, 18th ed. Mack Publishing Co., Easton, Pa. (1990), for information relating to aerosol administration, which is incorporated by reference herein for such teachings.

For delivery in liquid form, liquid formulations can be directly aerosolized and lyophilized powder can be aerosolized after reconstitution. For delivery in dry powder form, the formulation may be prepared as a lyophilized and milled powder. In addition, formulations may be delivered using a fluorocarbon formulation or other propellant and a metered dose dispenser. For delivery devices and methods, see, e.g., U.S. Pat. Nos. 4,137,914; 4,174,712; 4,524,769; 4,667,688; 5,672,581; 5,709,202; 5,672,581; 5,915,378; 5,997,848; 6,123,068; 6,123,936; and 6,397,838, each of which are herein incorporated by reference for such teachings.

A variety of powder inhalers and nebulizers are known in the art that can be used for A1PI administration. The delivery of A1PI formulations by inhalation are discussed, for example, in U.S. Pat. Nos. 5,093,316; 5,618,786; 5,780,014; 5,780,440; 6,655,379; 7,914,771; U.S. Patent Application Publication Nos. 2008/0078382 and 2008/0299049; and International Patent Application WO 01/34232, which are each incorporated by reference herein for such teachings.

In certain aspects, for example, nebulizers, which convert liquids into aerosols of a size that can be inhaled into the lower respiratory tract, are used, either in conjunction with a mask or a mouthpiece. Nebulizers suitable for use in certain aspects of the methods described herein can be either pneumatic or ultrasonic, and continuous or intermittent. Varieties of nebulizers suitable for use in the methods described herein are available commercially. Non-limiting examples of nebulizers are AKITA²® AIPIXNEP™ (Activaero), EFLOW®/TRIO® (PARI), (Activaero), PART LC STAR® (PARI), HALO-LITE® (Medic Aid), and others. Delivery devices that are capable of controlling and optimizing breathing patterns are advantageous for efficient delivery.

Nebulizers for liquid aerosol delivery may be categorized as jet nebulizers operated by a pressurized flow of air using a portable compressor or central air supply in a hospital, ultrasonic nebulizers incorporating a piezo-crystal to provide the energy for generating the aerosol out of an ultrasonic fountain, and electronic nebulizers based on the principle of a perforated vibrating membrane.

Nebulizers provide an increased amount of aerosol during inhalation while minimizing both aerosol losses during exhalation and the residual drug in the nebulizer reservoir. Nebulizers typically include an aerosol generator that atomizes the liquid through a vibrating diaphragm into particle sizes that are efficiently delivered to the lungs. Studies by Brand et al. in 2003 and 2009 discuss aerosolized pulmonary delivery of A1PI using a variety of nebulizers and administration devices, and both references are incorporated by reference herein for such teachings; Brand et al., *Eur. Resp. J.* 22(2): 263-267 (2003); Brand et al., *Eur. Respir. J.* 34(2): 354-360 (2009).

The operating conditions for delivery of a suitable inhalation dose will vary according to the type of mechanical device employed. For some aerosol delivery systems, such as nebulizers, the frequency of administration and operating period are dictated by the amount of the A1PI active composition per unit volume in the aerosol.

Generally, concentrated solutions of A1PI require less time to administer. Some devices, such as metered dose inhalers, may produce higher aerosol concentrations and consequently deliver an effective dose in a shorter period.

The nebulized dose is preferably aerosolized in droplets having a diameter of about 5 μm or less. In some aspects, the dose is aerosolized in droplets having a diameter of about 1-5 μm. Such droplet size enhances the A1PI deep lung deposition in the alveolar regions.

In some aspects, the diameter of the aerosolized droplets is at least about 0.5 μm, 1 μm, 2 μm, 3 μm, 4 μm, 5 μm, 6 μm, 7 μm, 8 μm, 9 μm, or 10 μm. In some aspects, the diameter of the aerosolized droplets is at least about 3.5 μm, 4 μm, 4.5 μm, 5 μm, 5.5 μm, 6 μm, 6.5 μm, 7 μm, or 7.5 μm. In other aspects, the diameter of the aerosolized droplets is no more than about 10 μm, 9 μm, 8 μm, 7 μm, 6 μm, 5 μm, 4 μm, 3 μm, 2 μm, or 1 μm.

In some aspects, at least about 50%, at least about 60%, at least about 70%, at least about 80%, or preferably at least about 90%, or preferably at least 95% or more of the dose of A1PI can be delivered to the lungs of a subject. In one aspect of the methods described herein, about 80-95% of the A1PI dose is delivered to the subject's lungs. In another aspect of the methods described herein, greater than 80% or more of the more of the dose of A1PI can be delivered to the lungs of a subject. The delivered dose may be the nominal dose, the effective dose, or the daily dose.

Certain aspects of the methods described herein employ a nebulizer comprising a ready-to-use inhalation solution comprising therapeutically effective amount of A1PI. In some aspects, the ready-to-use liquid pharmaceutical composition is packed in pre-sterilized units containing 0.25-1 mL, or 0.25-5 mL, 0.25-10 mL, or 0.25-20 mL of A1PI as ready to use solutions for inhalation. The ready-to-use units can be made of glass, polyethylene, or any other containers suitable for use with nebulization apparati.

In some aspects of the methods described herein, the ready-to-use liquid pharmaceutical composition is packed in pre-sterilized units containing 0.25 mL, 0.5 mL, 0.75 mL, 1.0 mL, 2.0 mL, 5.0 mL, 10 mL, 20 mL, 25 mL, or greater volumes of A1PI at various concentrations.

A1PI can be used for delaying the onset or progression of pulmonary exacerbations in a subject in need thereof by the daily administration of an effective amount of inhaled A1PI.

A1PI can be used for delaying the onset or progression of pulmonary disease in a subject in need thereof by the daily administration of an effective amount of inhaled A1PI.

A1PI can be used for the maintenance of a pulmonary disease-free state by the daily administration of an effective amount of inhaled A1PI.

As described herein, A1PI is periodically administered prior to exacerbation episodes. The exacerbations may be associated with various pulmonary diseases or disorders. Thus, one aspect of the methods described herein comprises administering to a subject in need thereof an effective amount of aerosolized A1PI via inhalation. Regular administration of an effective amount of aerosolized A1PI by inhalation is therapeutically effective in delaying the onset of or diminishing the progression of pulmonary exacerbations associated with pulmonary diseases or disorders.

Subjects with elevated risk for pulmonary exacerbations suitable for A1PI maintenance therapy typically have one or more of (a) an elevated risk for acute pulmonary exacerbation; (b) a significant decline of respiratory function; (c) a history of pulmonary exacerbations associated with cystic fibrosis, COPD, AATD, emphysema, asthma, mycobacterial infection, pneumonia, bronchiectasis, or chronic bronchitis; or environmental risk factors such as smoking history, allergies, occupational exposure to pulmonary irritants and/or exposure to air pollution.

Subjects with age 12 and older with an elevated risk for acute pulmonary exacerbation; a significant decline of respiratory function; a history of pulmonary exacerbations associated with cystic fibrosis, COPD, AATD, emphysema, asthma, mycobacterial infection, pneumonia, bronchiectasis, or chronic bronchitis; or environmental risk factors such as smoking history, allergies, occupational exposure to pulmonary irritants and/or exposure to air pollution are generally more susceptible to pulmonary exacerbations. The risk of pulmonary exacerbations typically increases with the subject's age. See FIG. 3 for exacerbation incidence as a function of age in CF patients.

Subjects with elevated risk for pulmonary exacerbations suitable for A1PI maintenance therapy can be identified by evaluating or identifying one or more of the prospective subject's: age; history of exacerbations; lung function ($FEV_1$); chronic productive cough (mucus producing); upper and lower airways' infectious pathogen burden; expiratory gas markers of respiratory inflammation; response to exogenous challenge testing for airways hyperresponsiveness; number and classes of concomitant medications; a genetic risk profile for respiratory disease; or environmental risks factors such as smoking history, allergies, occupational exposure to pulmonary irritants, and/or exposure to air pollution.

Pulmonary exacerbations are associated with increased severity of exacerbations; increased frequency of exacerbations; decreased lung function; decreased $FEV_1$; increased pulmonary tissue loss; decreased A1PI levels; increased pulmonary elastase levels; increased pulmonary infections; increased pulmonary bacterial load; increased antibiotic use; increased steroid use; increased cardiac dysrhythmia; increased morbidity and a decreased quality of life.

Regular administration of an effective amount of aerosolized A1PI by inhalation increases pulmonary and systemic A1PI levels, reduces neutrophil elastase levels, reduces pulmonary infections and bacterial loads, reduces inflammation, and reduces cardiac dysrhythmia. In addition, regular administration of A1PI reduces subjects' need for steroids, antibiotics mucolytics, and/or expectorants. Further, regular administration of an effective amount of aerosolized A1PI by inhalation can increase or improve lung function and/or diminish further progression of lung tissue deterioration. As such, regular administration of an effective amount of aerosolized A1PI by inhalation can alter the course of pulmonary diseases or disorders by delaying the onset of or diminishing the progression of pulmonary exacerbations and the symptoms associated therewith.

Specific benefits can include reduced hospitalization; reduced intensive care or mechanical ventilation need; reduced healthcare utilization or burden; reduced absences from school or work; decreased antibiotic need; decreased steroid need; and decreased relapse frequency. The reduction of pulmonary exacerbations resulting from regular administration of an effective amount of aerosolized A1PI by inhalation is typically associated with decreased morbidity and an improved quality of life for subjects.

Typically, inhaled A1PI is periodically administered from time to time as required to deliver an effective dose. The size of an effective dose of A1PI administered by inhalation depends on the form of A1PI used (i.e., liquid or dry powder), the volume to be inhaled, and, in the case of a liquid, the solubility and concentration of the A1PI.

A non-limiting example of an effective dose is between about 25 mg to about 750 mg A1PI per day. Alternatively, an effective dose of A1PI is between about 0.5 mg A1PI per kg of body weight per day to about 15 mg per kg of body weight per day (mg/kg/day), assuming a body weight of 50 kg. Doses for subjects with body weights less than or greater than 50 kg can be scaled up or down as required. The concentration and quantity of A1PI pharmaceutical composition administered to a subject depends on the efficiency of the inhalation delivery device, the periodicity of the administration, and the number of administration sessions per day.

In some aspects of the methods described herein, at least one dose of A1PI is about 0.01 mg, 0.05 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 3.0 mg, 4.0 mg, 5.0 mg, 6.0 mg, 7.0 mg, 8.0 mg, 9.0 mg, 10 mg, 15 mg, 20 mg, 25 mg, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, 350 mg, 360 mg, 370 mg, 380 mg, 390 mg, 400 mg, 410 mg, 420 mg, 430 mg, 440 mg, 450 mg, 460 mg, 470 mg, 480 mg, 490 mg, 500 mg, 510 mg, 520 mg, 530 mg, 540 mg, 550 mg, 660 mg, 770 mg, 880 mg, 990 mg, 600 mg, 610 mg, 620 mg, 630 mg, 640 mg, 650 mg, 660 mg, 670 mg, 680 mg, 690 mg, 700 mg, 710 mg, 720 mg, 730 mg, 740 mg, 750 mg, 760 mg, 770 mg, 780 mg, 790 mg, 800 mg, 810 mg, 820 mg, 830 mg, 840 mg, 850 mg, 860 mg, 870 mg, 880 mg, 890 mg, 900 mg, 910 mg, 920 mg, 930 mg, 940 mg, 950 mg, 960 mg, 970 mg, 980 mg, 990 mg, 1000 mg, or in some aspects, even more.

In some aspects of the methods described herein, an effective dose of A1PI is at least about 0.5 mg, 1 mg, 2 mg, 3, mg, 4, mg, 5 mg, 6 mg, 7 mg, 8 mg 9 mg, 10 mg 15 mg, 20 mg, 25 mg, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, 350 mg, 360 mg, 370 mg, 380 mg, 390 mg, 400 mg, 410 mg, 420 mg, 430 mg, 440 mg, 450 mg, 460 mg, 470 mg, 480 mg, 490 mg, 500 mg, 510 mg, 520 mg, 530 mg, 540 mg, 550 mg, 560 mg, 570 mg, 580 mg, 590 mg, 600 mg, 610 mg, 620 mg, 630 mg, 640 mg, 650 mg, 660 mg, 670 mg, 680 mg, 690 mg, 700 mg, 710 mg, 720 mg, 730 mg, 740 mg, 750 mg, 760 mg, 770 mg, 780 mg, 790 mg, 800 mg, 810 mg, 820 mg, 830 mg, 840 mg, 850 mg, 860 mg, 870 mg, 880 mg, 890 mg, 900 mg, 910 mg, 920 mg, 930 mg, 940 mg, 950 mg, 960 mg, 970 mg, 980 mg, 990 mg, 1000 mg, or in some aspects, even more.

In some aspects of the methods described herein, at least one individual dose of A1PI is no more than about 1000 mg, 990 mg, 980 mg, 970 mg, 960 mg, 950 mg, 940 mg, 930 mg, 920 mg, 910 mg, 900 mg, 890 mg, 880 mg, 870 mg, 860 mg, 850 mg, 840 mg, 830 mg, 820 mg, 810 mg, 800 mg, 790 mg, 780 mg, mg, 770 mg, 760 mg, 750 mg, 740 mg, 730 mg, 720 mg, 710 mg, 700 mg, 690 mg, 680 mg, 670 mg, 660 mg, 650 mg, 640 mg, 630 mg, 620 mg, 610 mg, 600 mg, 590 mg, 580 mg, 570 mg, 560 mg, 550 mg, 540 mg, 530 mg, 520 mg, 510 mg, 500 mg, 490 mg, 470 mg, 460 mg, 450 mg, 440 mg, 430 mg, 420 mg, 410 mg, 400 mg, 390 mg, 380 mg, 370 mg, 360 mg, 350 mg, 340 mg, 330 mg, 320 mg, 310 mg, 300 mg, and in some aspects, even less.

In some aspects of the methods described herein, at least one individual dose of A1PI is about 1000 mg, 990 mg, 980 mg, 970 mg, 960 mg, 950 mg, 940 mg, 930 mg, 920 mg, 910 mg, 900 mg, 890 mg, 880 mg, 870 mg, 860 mg, 850 mg, 840 mg, 830 mg, 820 mg, 810 mg, 800 mg, 790 mg, 780 mg, 770 mg, 760 mg, 750 mg, 740 mg, 730 mg, 720 mg, 710 mg, 700 mg, 690 mg, 680 mg, 670 mg, 660 mg, 650 mg, 640 mg, 630 mg, 620 mg, 610 mg, 600 mg, 590 mg, 580 mg, 570 mg, 560 mg, 550 mg, 540 mg, 530 mg, 520 mg, 510 mg, 500 g, 490 mg, 480 mg, 470 mg, 460 mg, 450 mg, 440 mg, 430 mg, 420 mg, 410 mg, 400 mg, 390 mg, 380 mg, 370 mg, 360 mg, 350 mg, 340 mg, 330 mg, 320 mg, 310 mg, 300 mg, 290 mg, 280 mg, 270 mg, 260 mg, 250 mg, 240 mg, 230 mg, 220 mg, 210 mg, 200 mg, 190 mg, 180 mg, 170 mg, 160 mg, 150 mg, 140 mg, 130 mg, 120 mg, 110 mg, 100 mg, 90 mg, 80 mg, 70 mg, 60 mg, 50 mg, 40 mg, 30 mg, 25 mg, 20 mg, 15 mg, 10 mg, 9.0 mg, 8.0 mg, 7.0 mg, 5.0 mg, 4.0 mg, 3.0 mg, 2.0 mg, 1.0 mg, 0.5 mg, 0.1 mg, and even, in some aspects, less than about 0.1 mg.

In some aspects of the methods described herein, an mg/kg effective dose of A1PI is at least about 0.01 body weight to about 20 mg/kg body weight per day.

In some aspects of the methods described herein, an effective daily dose of A1PI is at least about 0.01 mg/kg, 0.05 mg/kg, 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2.0 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, 3.0 mg/kg, 3.1 mg/kg, 3.2 mg/kg, 3.3 mg/kg, 3.4 mg/kg, 3.5 mg/kg, 3.6 mg/kg, 3.7 mg/kg, 3.8 mg/kg, 3.9 mg/kg, 4.0 mg/kg, 4.1 mg/kg, 4.2 mg/kg, 4.3 mg/kg, 4.4 mg/kg, 4.5 mg/kg, 4.6 mg/kg, 4.7 mg/kg, 4.8 mg/kg, 4.9 mg/kg, 5.0 mg/kg, 5.1 mg/kg, 5.2 mg/kg, 5.3 mg/kg, 5.4 mg/kg, 5.5 mg/kg, 5.6 mg/kg, 5.7 mg/kg, 5.8 mg/kg, 5.9 mg/kg, 6.0 mg/kg, 6.1 mg/kg, 6.2 mg/kg, 6.3 mg/kg, 6.4 mg/kg, 6.5 mg/kg, 6.6 mg/kg, 6.7 mg/kg, 6.8 mg/kg, 6.9 mg/kg, 7.0 mg/kg, 7.1 mg/kg, 7.2 mg/kg, 7.3 mg/kg, 7.4 mg/kg, 7.5 mg/kg, 7.6 mg/kg, 7.7 mg/kg, 7.8 mg/kg, 7.9 mg/kg, 8.0 mg/kg, 8.1 mg/kg, 8.2 mg/kg, 8.3 mg/kg, 8.4 mg/kg, 8.5 mg/kg, 8.6 mg/kg, 8.7 mg/kg, 8.8 mg/kg, 8.9 mg/kg, 9.0 mg/kg, 9.1 mg/kg, 9.2 mg/kg, 9.3 mg/kg, 9.4 mg/kg, 9.5 mg/kg, 9.6 mg/kg, 9.7 mg/kg, 9.8 mg/kg, 9.9 mg/kg, 10.0 mg/kg, 10.1 mg/kg, 10.2 mg/kg, 10.3 mg/kg, 10.4 mg/kg, 10.5 mg/kg, 10.6 mg/kg, 10.7 mg/kg, 10.8 mg/kg, 10.9 mg/kg, 11.0 mg/kg, 11.1 mg/kg, 11.2 mg/kg, 11.3 mg/kg, 11.4 mg/kg, 11.5 mg/kg, 11.6 mg/kg, 11.7 mg/kg, 11.8 mg/kg, 11.9 mg/kg, 12.0 mg/kg, 12.1 mg/kg, 12.2 mg/kg, 12.3 mg/kg, 12.4 mg/kg, 12.5 mg/kg, 12.6 mg/kg, 12.7 mg/kg, 12.8 mg/kg, 12.9 mg/kg, 13.0 mg/kg, 13.1 mg/kg, 13.2 mg/kg, 13.3 mg/kg, 13.4 mg/kg, 13.5 mg/kg, 13.6 mg/kg, 13.7 mg/kg, 13.8 mg/kg, 13.9 mg/kg, 14.0 mg/kg, 14.1 mg/kg, 14.2 mg/kg, 14.3 mg/kg, 14.4 mg/kg, 14.5 mg/kg, 14.6 mg/kg, 14.7 mg/kg, 14.8 mg/kg, 14.9 mg/kg, 15.0 mg/kg, 15.1 mg/kg, 15.2 mg/kg, 15.3 mg/kg, 15.4 mg/kg, 15.5 mg/kg, 15.6 mg/kg, 15.7 mg/kg, 15.8 mg/kg, 15.9 mg/kg, 16.0 mg/kg, 16.1 mg/kg, 16.2 mg/kg, 16.3 mg/kg, 16.4 mg/kg, 16.5 mg/kg, 16.6 mg/kg, 16.7 mg/kg, 16.8 mg/kg, 16.9 mg/kg, 17.0 mg/kg, 17.1 mg/kg, 17.2 mg/kg, 17.3 mg/kg, 17.4 mg/kg, 17.5 mg/kg, 17.6 mg/kg, 17.7 mg/kg, 17.8 mg/kg, 17.9 mg/kg, 18.0 mg/kg, 18.1 mg/kg, 18.2 mg/kg, 18.3 mg/kg, 18.4 mg/kg, 18.5 mg/kg, 18.6 mg/kg, 18.7 mg/kg, 18.8 mg/kg, 18.9 mg/kg, 19.0 mg/kg, 19.1 mg/kg, 19.2 mg/kg, 19.3 mg/kg, 19.4 mg/kg, 19.5 mg/kg, 19.6 mg/kg, 19.7 mg/kg, 19.8 mg/kg, 19.9 mg/kg, 20.0 mg/kg of body weight per day, or in some aspects, even more.

As a non-limiting example, a typical inhaled A1PI administration period lasts generally between about 1-5 minutes, 5-10 minutes, 10-20 minutes, 20-30 minutes, 30-40 minutes, 40-50 minutes, or 50-60 minutes, but may be as long as about 120-180 minutes, depending on the subject, the delivery apparati, the A1PI concentration and/or volume, the effective dose and/or the daily dose.

In some aspects of the methods described herein, A1PI may be inhaled for about 0.5 min, 1 min, 2 min, 5 min, 10 min, 15 min, 20 min, 25 min, 30 min, 35 min, 40 min, 45 min, 50 min, 55 min, 60 min, 70 min, 80 min, 90 min, 100 min, 120 min, 150 min, 180 min, or in some aspects even longer.

In some aspects, A1PI is administered by a clinician. In other aspects, A1PI is self-administered. For example, A1PI may be administered in the morning, in the afternoon, or periodically throughout the day. The dose size may be adjusted to account for the frequency and timing of administration of the A1PI, and that the daily dosage may, to some degree, be determined by the subject or a clinician based on estimated need, on the delivery system used, and on the presence or absence of other risk factors (e.g., hereditary risk factors or other environmental risk factors such as occupational risk factors and/or exposure to air pollution).

In some aspects, it may be desirable to place an upper limit on single doses and/or daily dosage. Administration devices that limit or modulate self-administration of pulmonary administered pharmaceuticals and other substances in order to prevent possible overdose by the subject are known in the art.

In some aspects of the methods described herein, A1PI may be administered several times a month, several times a week, once each day, or even several times a day. Typically, a therapeutically effective dose is administered once each day. As a non-limiting example, an effective dose may be administered in one or more sessions, such as one portion of a dose is administered in the morning and the remaining portion of a dose is administered in the afternoon. Alternatively, an entire dose may be administered in one session. In some cases, 3-4 or more administrations per day may be required to achieve an effective dose of A1PI and/or delaying the onset of or diminishing the progression of pulmonary exacerbations.

Dose frequency may be from once daily, twice daily, three times daily, or four times daily, to twice daily, four times daily, six times daily, eight times daily, or more than eight times per day. In some aspects, the dose frequency is from once daily to six times daily, once daily to four times daily, twice daily, or once daily. Frequency of administration may be determined and adjusted over the course of care, and is generally, but not necessarily, based on symptoms and clinical findings. In the case of delaying the onset of or diminishing the progression of pulmonary exacerbations and the symptoms associated therewith, in a subject exposed to environmental conditions that increase the likelihood of an exacerbation, the frequency of administration may be modulated based on the frequency and/or severity of exposure.

In some aspects, a bronchodilator can be administered in common formulation with A1PI, or functionally active portion or fusion thereof. In other aspects, the bronchodilator is administered in a composition separate from that containing A1PI or functionally active portion or fusion thereof. In some of these latter aspects, the bronchodilator is administered by inhalation on a dosage schedule that is the same as the dosage schedule for administration of A1PI or functionally active portion or fusion thereof. In others of these aspects, the bronchodilator is administered on a different dosage schedule from that used for A1PI or functionally active portion or fusion thereof. In various aspects, the bronchodilators are administered orally.

In various aspects, the bronchodilator is selected from bronchodilators currently in clinical use for treatment of respiratory exacerbations. The bronchodilator can be one or more of Fenoterol; Salbutamol (albuterol); Terbutaline; Formoterol; Salmeterol; Ipratropium bromide; Oxitropium bromide; Tiotropium; Fenoterol/Ipratropium; Salbutamol/Ipratropium; Aminophylline; Theophylline; or other bronchodilators known in the art.

In some aspects, a corticosteroid is administered can be administered with the A1PI. In some aspects, a corticosteroid is administered in a common formulation with A1PI, or functionally active portion or fusion thereof. In other aspects, the corticosteroid is administered in a composition separate from that containing A1PI or functionally active portion or fusion thereof. In some of aspects, the corticosteroid is administered by inhalation on a dosage schedule that is the same as the dosage schedule for administration of A1PI or functionally active portion or fusion thereof. In others of these aspects, the corticosteroid is administered on a different dosage schedule from that used for A1PI or functionally active portion or fusion thereof. In various aspects, the corticosteroids are administered orally.

In various aspects, the corticosteroid is selected from corticosteroids currently in clinical use for treatment of respiratory exacerbations. The corticosteroid can be one or more of Beclomethasone; Budesonide; Fluticasone; Triamcinolone; Formoterol/Budesonide combination; Salmeterol/Fluticasone combination; Prednisone; or Methyl-prednisolone or other corticosteroids known in the art.

Corticosteroids useful in various aspects of the methods described herein include, for example, beclomethasone dipropionate, triamcinolone acetonide, or fluticasone propionate. In various aspects, combinations of corticosteroids are used.

In other aspects, the methods further comprise administration of one or more of mucolytics/expectorants for mucus regulation, anti-oxidants, and antibiotics for the management of infection, if present.

In one aspect, an anti-oxidant excipient may be required to protect the A1PI from the effect of active smoking or other oxidant stress. Useful antioxidants include vitamin E (alpha-, beta-, gamma-, and delta-tocopherols and/or alpha-, beta-, gamma-, and/or delta-tocotrienols), vitamin C (ascorbic acid), beta-carotene, glutathione (GSH), melatonin, selenium, superoxide dismutase, catalase, and peroxiredoxins.

In other aspects, the methods described herein reduce the subject's need for and exposure to steroids, antibiotics, bronchodilators, mucolytics, and/or expectorants.

In another embodiment, kits for delaying the onset or progression of pulmonary exacerbations are described. In one aspect, the kits comprise at least one dose of at least one composition for use in the methods described herein. In certain aspects, for example, the kit comprises at least one daily dose or at least one effective dose of A1PI in an individual container.

In some aspects, the kit further comprises at least one device for delivering at least one dose by inhalation. For example, the kit may comprise a nebulizer suitable for aerosolization of the composition. In other aspects, the kit comprises a metered dose inhaler. In other aspects, the kit comprises a metered dose inhaler. The one or more doses may be prior-loaded into the delivery device or may be separately packaged.

In aspects comprising a nebulizer, the one or more doses may be liquid. In other aspects comprising a nebulizer, the one or more doses may be dry, and the kit further comprises sterile diluent to be used to rehydrate the dried composition. The sterile diluent typically will be separately packaged in a container that maintains sterility, such as an ampule or vial. In various aspects, the diluent is selected from the group comprising sterile water, saline, dextrose solution, D5 normal saline, and Ringer's solution.

In aspects comprising a metered dose inhaler, the metered dose inhaler may be prior-loaded with at least one dose of the compositions described herein. Typically, the metered dose inhaler will be prior-loaded with a plurality of doses. In certain other aspects, the metered dose inhaler is packaged separately from the composition, with a plurality of doses typically present within a cartridge dimensioned to engage within the metered dose inhaler.

In aspects comprising a dry powder inhaler, the metered dose inhaler may be prior loaded with one or more doses of dry composition, or in other aspects is separately packaged from one or more dry powder doses.

Various aspects of the kits described herein further comprise a set of instructions for use of the included composition. The instructions may inform the user of methods for administration of the compositions described herein, suggested dosages, schedules for levels of exposure to environmental conditions that may promote exacerbation (such as smoking or air pollution), precautions, expected results, warnings, and the like. The instructions may be in any form, and provided as a separate insert or on a label affixed to the container or packaging. Instructions include procedures for any of the methods described herein.

The instructions may also include diagnostic criteria for clinicians, including methods for identifying subjects with elevated risk for pulmonary exacerbations suitable for A1PI maintenance therapy, such as subject's age, history of exacerbations, lung function ($FEV_1$), chronic productive cough (mucus producing), upper and lower airways' infectious pathogen burden, expiratory gas markers of respiratory inflammation, response to exogenous challenge testing for airways hyperresponsiveness, number and classes of concomitant medications, genetic risk profile for respiratory disease, smoking history, and exposure to occupational or environmental variables such as allergies, pollution, and respiratory irritants.

In some aspects, instructions are directed to the use of A1PI by inhalation delaying the onset or progression of pulmonary exacerbations. In some aspects, instructions are directed to the use of A1PI by inhalation in delaying the onset or progression of pulmonary exacerbations associated with cystic fibrosis, $alpha_1$-antitrypsin deficiency, or COPD. In some aspects, instructions are directed to the use of A1PI by inhalation in delaying the onset or progression of pulmonary exacerbations associated with emphysema, asthma, mycobacterial infection, pneumonia, bronchiectasis, or chronic bronchitis.

In some aspects, the kits further include one or more additional agents, as described herein, for delaying the onset or progression of pulmonary exacerbations, including one or more bronchodilators, one or more corticosteroids, and/or one or more mucolytics, expectorants, antioxidants, or antibiotics.

Safety and Tolerability of A1PI

The safety and tolerability of inhaled A1PI is supported by several studies conducted with inhaled PROLASTIN®. Inhaled PROLASTIN® has been investigated in 12 clinical studies in healthy volunteers, asthma patients, AATD patients, and CF patients. Single dose and repeat dose studies of up to 28-days were performed. In addition, five investigator-initiated clinical studies administered PROLASTIN® A1PI by inhalation to healthy volunteers, AATD subjects, and CF subjects. These five studies included repeated doses from 1-to-8 weeks. Almost 300 subjects (291 subjects: 65 healthy, 134 CF subjects, 76 AATD subjects, and 16 asthmatics) have received various inhaled doses of PROLASTIN®. See Table 1. Only two subjects reported Serious Adverse Events (SAEs) resulting from A1PI administration. One subject experienced dyspnea and one subject experienced increased cough and increased sputum. Collectively, inhaled PROLASTIN® has been shown to be safe and well tolerated.

Aerosolized PROLASTIN® has been administered at doses ranging from a single 50 mg dose to 350 mg twice daily (i.e., 700 mg/day) with the majority of doses being in the 100 to 200 mg rage administered once or twice per day. Dose durations ranged from 1-day up to 56 days. Griese et al., *Eur. Resp. J.* 29(2): 240-250 (2008); Griese et al., *Electrophoresis* 22(1): 165-171 (2001). Per-subject total dose exposures have ranged from 50 mg over 1-day; 5,600 mg over 14-days; 11,200 mg over 56-days (Griese et al., *Electrophoresis* 22(1): 165-171 (2001)); and up to 19,600 mg over 28-days (Berger et al., *Pediatric Pulmonol.* 20: 421 (1995)). These studies used various nebulizers; therefore, the portion of dose that actually reached the lungs likely varied.

In studies of inhaled PROLASTIN® to date, only one study reported SAEs. Berger et al., *Pediatric Pulmonol.* 20: 421 (1995). In this open label, dose escalation study, 26 CF subjects with $FEV_1 \geq 60\%$ of predicted received 100 mg, 200 mg, or 350 mg of aerosolized PROLASTIN® twice daily for 4-weeks. Per-subject total aerosol PROLASTIN® exposure at the highest dose was approximately 19,600 mg over 28-days. There were four SAEs in three subjects in this study. One subject in the 200 mg dose group discontinued the study on Day 11 due to shortness of breath (dyspnea). Another subject in the 200 mg dose group had two emergent SAEs of increased cough and sputum on Day 25, which were possibly related to PROLASTIN®. This subject continued inhaling PROLASTIN® through Day 28 and received remedial therapy on Day 29. The fourth SAE in this study was a fainting episode in a subject assigned to the 350 mg dose group. This subject was removed from the study prior to receiving any study drug.

TABLE 1

Summary of A1PI Studies

| Author | Subjects,[1] Duration of Dosing | Dose, Device | Outcomes |
|---|---|---|---|
| Cystic Fibrosis | | | |
| McElvaney et al. | 12 subjects,[2] 1 week | 1.5-3.0 mg/kg/BID, Not reported | Effectively delivered *Pseudomonas* killing ELF threshold identified |
| Berger et al. | 22 subjects, 4 weeks | 100, 200, 350 mg BID, PARI Master/ PARI-LL | Effectively delivered Dose ranging information |
| Calvete et al. | 4 subjects, 8 days | 3.0 mg/kg BID PARI Master and CR-60 | Anti-NE activity significantly increased |
| Griese et al. | 8 subjects, 8 weeks | 100 mg BID, PARI Master/ PARI-LC Plus | Reduced BAL protein content |
| Cantin et al. | 17 subjects, 10 days | 250 mg BID, PARI-LC Plus | High dose exposure well tolerated Suggested reduced *Pseudomonas* burden |

TABLE 1-continued

Summary of A1PI Studies

| Author | Subjects,[1] Duration of Dosing | Dose, Device | Outcomes |
|---|---|---|---|
| Griese et al. | 52 subjects, 4 weeks | 25 mg QD, AKITA/PARI-LC Plus | No reduction in elastase Low dose exposure Effective irrespective of site of delivery Reduced sputum neutrophils Reduced *Pseudomonas* burden Reduced cytokine levels |
| Kerem[3] | 14 subjects[4] 28 days | 80 mg QD, PARI eFlow | Reduced sputum neutrophils Reduced NE |
| Alpha$_1$-antitrypsin Deficiency/COPD | | | |
| Lieberman[5] | 96 subjects | Post hoc survey of AATD patients receiving A1PI infusions for 1-10 years | Reduced frequency and severity of lung infections |
| Dirksen et al. | 77 subjects, 2-2.5 years | Intravenous A1PI 60 mg/kg/week | Reduced severity of exacerbations; no effect on frequency |

McElvaney et al. *Lancet* 337(8738): 392-394 (1991); Berger et al., *Pediatric Pulmonol.* 20: 421 (1995); Calvete et al., *An. Esp. Pediatr.* 44(2): 109-111 (1996; Spanish); Griese et al., *Electrophoresis* 22(1): 165-171 (2001); Cantin et al., *Clin. Invest. Med.* 29(4): 201-207 (2006); Griese et al., *Eur. Resp. J.* 29(2): 240-250 (2008); Kerem et al., *Am. J. Respir. Crit. Care. Med.* 179: A1185 (2009); Lieberman, *Chest* 118: 1480-1485 (2000); Dirsken et al., *Eur. Resp. J.* 33: 1345-1353 (2009).
[1]Number of subjects who received aerosolized A1PI upon which reported study results were based.
[2]Number of subjects receiving aerosolized A1PI; five additional subjects received IV A1PI.
[3]This study was conducted with Kamada's pd-A1PI.
[4]Subjects were randomized 2:1 to 80 mg per day of inhaled A1PI or placebo; seven additional subjects received placebo.
[5]This study did not indicate the source of A1PI used by patients.

The studies in Table 1 showed that acute A1PI therapy reduced the severity of acute pulmonary exacerbations. This was based on a reduction of inflammation markers and favorable changes in pulmonary bacterial colony counts. However, the relatively brief duration of A1PI exposure in small populations, the use of unproven surrogate endpoints, and the variation in design, significantly limits the utility of these data in predicting outcomes for delaying the onset or diminishing the progression of pulmonary exacerbations in a subject, as described herein. Moreover, none of the studies in Table 1 assessed the efficacy of long-term A1PI-maintenance therapy, as described herein. Pulmonary exacerbations are typically viewed and treated as discrete episodic events, rather than a disease course or continuum that progressively worsens. None of these studies in Table 1 evaluated the outcome(s) of A1PI maintenance therapy on diminishing the progression or inhibiting successive lung tissue damage (measured by $FEV_1$, for example) resulting from frequent or recurrent exacerbations. Improved therapy that delays the onset or diminishes the progression of pulmonary exacerbations a priori is desirable. A1PI maintenance therapy can reduce a subject's need for and exposure to steroids, antibiotics, bronchodilators, mucolytics, and/or expectorants. In addition, improved therapy that delays the onset or diminishes the progression of pulmonary exacerbations can halt the progressive destruction of lung tissue and progressive diminution of lung function as demonstrated by markers such as $FEV_1$, among others. Accordingly, studies for evaluating the efficacy of long-term A1PI maintenance therapy to delay the onset of or diminish the progression of pulmonary exacerbations a priori are described herein. Also described are methods for determining subjects in need of A1PI maintenance therapy and methods for evaluating the outcomes.

A1PI can be administered by inhalation periodically or from time-to-time each day over periods of many days, weeks, months, years, multiple years, or decades to delay the onset or progression of pulmonary exacerbations. Regular inhalation A1PI maintenance therapy, comprising daily A1PI administration, can be carried out using the methods described herein to delay the onset of or diminish the progression of pulmonary exacerbations in a subject. The incidence of pulmonary exacerbations, the frequency among pulmonary exacerbations, and the severity of pulmonary exacerbations may be diminished in a subject using regular inhalation A1PI maintenance therapy as described herein.

Regular inhalation A1PI maintenance therapy, comprising daily A1PI administration, over an infinite period, can delay the onset or diminish the progression of pulmonary exacerbations throughout that period. Pulmonary exacerbations may be eliminated in subjects using long-term, regular A1PI maintenance therapy.

EXAMPLES

Example 1

Purification of Alpha$_1$-Proteinase Inhibitor

A non-limiting process for purifying alpha$_1$-proteinase inhibitor that includes a final hydrophobic interaction chromotography step is described in U.S. Patent Application Publication No. US 2011/0237781 A1, which is incorporated by reference herein for such teachings. A flow diagram of this purification process is shown in FIG. 2. A1PI purified using this method is referred to herein as "A1PI-HC." The upstream process used to manufacture A1PI-HC is based on Cohn plasma fractionation. The starting material for the purification process is Cohn Fraction IV-1 paste, which is suspended in a buffered solution and mixed until homogenous. Contaminating proteins are precipitated from the suspension by the addition of 11.5% PEG 3350 and are removed via centrifugation followed by depth filtration. The PEG supernatant/filtrate is mixed with polysorbate 20 (Tween® 20) and tri-n-butyl phosphate (TNBP) to inactivate enveloped viruses. Purification of the PEG supernatant/filtrate continues using anion exchange chromatography followed by ultrafiltration, diafiltration, and cation exchange chromatography. The cation exchange flow-through material is nano-filtered to remove enveloped and non-enveloped viruses, passed through a hydrophobic interaction column to remove residual, low-level impurities, and then ultrafiltered, diafiltered, and bulked. The bulk material is sterile filtered through 0.2 μm filters into sterile bags. Bulk A1PI-HC produced by this process may be frozen prior to filling. Bulk A1PI-HC products are sterile filtered into a sterile bulk tank and then aseptically filled and stored as a liquid at 2-8° C.

Example 2

Preclinical Studies with A1PI-HC

The preclinical toxicology of A1PI-HC was evaluated using acute and 28-day daily repeat dose studies where the nebulized A1PI was administered via inhalation. These studies were conducted in two species, Sprague Dawley rats (*Rattus norvegicus*) and cynomolgus monkeys (*Macaca fascicularis*). In addition, a 26-week chronic inhalation toxicity study with a 13-week interim sacrifice was conducted in rats. Results from these studies are summarized in Table 2.

TABLE 2

Nonclinical Overview of Inhaled Aerosolized A1PI-HC in Rats and Non-Human Primates

| Type of Study Species/Strain | Aerosol Admin. Method | Dosing Duration (minutes) | Dose (mg/kg/day) |
|---|---|---|---|
| Single-Dose Toxicity | | | |
| Inhalation Sprague Dawley Rat | Nose-only | 30, 60, 120, 240 | Target: 5, 10, 20, 40<br>Achieved: 6.16, 7.46, 18.8, 31.9 |
| Inhalation Cynomolgus monkey | Oronasal (mask) | From 10-44 dependent upon mean body weight | Target: 10, 20, 30, 40<br>Achieved: 10.5, 20.2, 29.6, 40.9 |
| Repeated-Dose Toxicity[1] | | | |
| 28-Day Inhalation Sprague Dawley Rat | Nose-only | 60, 120, 240 | Target: 10, 20, 40<br>Achieved[2]: 11.5, 22.1, <u>46.6</u> |
| 28-Day Inhalation Cynomolgus monkey | Oronasal (mask) | 8, 20, 35 dependent upon mean body weight | Target: 10, 20, 40<br>Achieved: 9.7, 20.9, <u>38.0</u> |
| 26-Week Inhalation + 13-Week Interim Sacrifice Rat: Sprague Dawley | Nose-only | 60, 120, 240 | Target: 10, 20, 40<br>Achieved: 11.0, 20.6, <u>46.4</u> |

[1]Unless otherwise specified, the highest No Observed Adverse Effect Level (NOAEL) is underlined for Repeated-Dose Toxicity.
[2]Achieved: Estimated achieved doses mean of males and females In all of the studies listed in Table 2, A1PI-HC was well tolerated and did not cause any significant toxicity at doses far exceeding those that may be administered to subjects. In the studies above, monkeys received approximately 38 mg/kg/day for up to 28 days, and rats received approximately 46 mg/kg/day for 26 weeks. As a non-limiting example of the methods described herein, subjects can typically receive approximately 2-15 mg/kg/day (100-200 mg/day).

Example 3

Advances in Inhalation Delivery Device Technology

Despite all the advantages of aerosol application, the development of this route of administration has been hampered by poor device efficiency and by the lack of inhalation systems that can deliver large proteins effectively to the peripheral airways. Previous devices required excessively long inhalation times and delivered widely varying amounts of A1PI, primarily to the central airways rather than the peripheral lung. New advances in inhalation delivery technology have created devices with more efficient and reproducible delivery to the lungs, such as the AKITA$^2$ nebulizer system. Brand et al., *Eur. Respir. J.* 34(2): 354-360 (2009).

A recent A1PI deposition study using the AKITA$^2$, a state of the art delivery device, characterized the homogeneity of deposition site of the drug within the lungs after a single inhalation of 2 mL (70 mg of A1PI) of $^{99}$mTc-labeled PROLASTIN®. Brand et al., *Eur. Respir. J.* 34: 354-360 (2009). In seven subjects with AATD, seven subjects with CF, and six healthy volunteers, the total lung deposition immediately after inspiration was about 70% of the filling volume of A1PI in the nebulizer. Extrathoracic deposition was in the range of 15% to 20%. The amount of A1PI remaining in the device was approximately 9%. The mean peripheral lung deposition exceeded 40% in all groups. Median inhalation time was 5.5 minutes for healthy volunteers, 7.7 minutes for patients with AATD, and 8.3 minutes for CF patients. Data are summarized in Table 3.

TABLE 3

Regional Deposition in the lung of inhaled Prolastin ® in healthy volunteers, alpha$_1$-antitrypsin deficiency (AATD) subjects, and cystic fibrosis subjects [1]

| Regional Deposition | Healthy Volunteers N = 6 | AATD Patients N = 7 | Cystic Fibrosis Patients N = 7 |
| --- | --- | --- | --- |
| Central deposition (%) | 29.4 ± 4.8 | 30.3 ± 4.3 | 27.3 ± 4.7 |
| Peripheral deposition (%) | 40.9 ± 4.5 | 42.3 ± 6.6 | 43.3 ± 5.3 |
| Total deposition (%) | 70.3 ± 7.9 | 72.6 ± 3.2 | 70.6 ± 5.8 |

[1] Source: Brand et al., *Eur. Respir. J.* 34: 354-360 (2009).

The AKITA[2], manufactured by Activaero GmbH in Gemünden, Germany (utilized in the study described in Table 3), is used in the clinical development of inhaled A1PI-HC. This newer, more advanced nebulizer system produces 5-times greater deposition of study drug compared to older nebulizer systems (e.g., ULTRAVENT® nebulizer, PARI MASTER® compressor). This nebulizer system produces greater peripheral deposition, reduces the required duration of inhalation times, lowers the variability of nebulization, and allows more accurate dosing that is independent of lung function impairment. Brand et al., *Eur. Respir. J.* 34(2): 354-360 (2009).

Example 4

Safety, Efficacy, and Tolerability of A1PI-HC in CF

An exemplary program assessing inhaled A1PI-HI maintenance therapy for delaying the onset or diminishing the progression of pulmonary exacerbations in cystic fibrosis patients is described. Similar programs are envisioned and are applicable for COPD, AATD, asthma, emphysema, or other pulmonary disorders. The CF program includes three studies to assess the safety, efficacy, and tolerability of inhaled A1PI-HC maintenance therapy as described herein.

A1PI Dose Escalation

The first study is a three-week dose escalation experiment, to assess the safety and tolerability of daily inhaled A1PI-HC at two different doses (100 mg and 200 mg). Each cohort of this experiment enrolls approximately 15 subjects: 10 subjects on A1PI-HC and 5 subjects on placebo, for a total enrollment of approximately 30 subjects. Several biomarkers are studied as exploratory markers of dose adequacy and efficacy. The placebo for these studies is composed of the same excipients present in the study drug. Polysorbate 80 (0.01% w/v) is added in order to mimic foaming properties of A1PI-HC.

The dose escalation experiments are expected demonstrate that inhaled A1PI-HC delays the onset of or diminishes the progression of symptomatic pulmonary exacerbations in CF subjects, particularly those requiring therapeutic intervention. In addition, these experiments can establish the safety of aerosolized A1PI-HC over a three-week period of daily exposure. A subpopulation of CF subjects with increased risk for these exacerbations is used in this experiment. Data from the U.S. Cystic Fibrosis Foundation Registry indicates a low risk for multiple exacerbations in patients below the age of 11. See FIG. 3. Subjects are questioned at screening regarding their history of exacerbations within the prior year.

The dose escalation study is accomplished using two sequential cohorts of subjects. In the first cohort, a total of 15 subjects aged 12 or older are randomized in a ratio of 2:1 to either A1PI-HC 100 mg or a matching placebo delivered once daily via nebulizer. Both subjects and investigators are blinded as to assignment. At the conclusion of 21 days of dosing, subjects are followed for an additional 28-day safety-monitoring period. The results of this portion of the experiment are assessed for safety prior to initiating the second cohort of the study.

Subjects in the second cohort of the study receive A1PI-HC 200 mg administered by daily aerosol. A total of 15 subjects aged 12 or older will be randomized in a ratio of 2:1 to either A1PI-HC 200 mg or a matching placebo delivered once daily via nebulizer. No subjects from the first cohort of the experiment will participate in the second cohort.

Collectively, safety data can be obtained for approximately evaluable subjects, comprising about 10 at each dose level. Subjects are actively monitored for safety by serial spirometry, physical exam, AE assessment, blood and urine testing, and weekly phone calls. All subjects are tested for the presence of antibodies to A1PI-HC at initial screening and the conclusion of the monitoring period.

Long Term Safety and Efficacy of A1PI

The long-term safety and efficacy experiment examines the efficacy and safety of A1PI (100 mg and 200 mg daily aerosol A1PI-HC) compared to placebo over a six-moth period. Approximately 186 subjects are randomized 1:1:1 among each of the active arms and placebo (100 mg per day; 200 mg per day; or daily placebo). The primary efficacy endpoint is the frequency of acute respiratory exacerbations experienced by the subjects receiving active A1PI versus those on placebo. Biomarkers and patient reported outcomes constitute secondary endpoints.

The proposed criteria identifying an acute exacerbation is a subject presenting with 4 out of 12 signs or symptoms according to the Fuchs' criteria and requiring treatment with an unscheduled course of a systemic or aerosolized antibiotic given at the discretion of the subject's physician. See below; Fuchs et al., *N. Engl. J. Med.* 331(10): 637-42 (1994). In addition, signs and/or symptoms that appear to constitute an exacerbation are collected and analyzed separately. Subjects will forego scheduled systemic antibiotics (with the exception of oral azithromycin) during the course of the experiment. Scheduled aerosolized antibiotics are permitted. Selection of other efficacy endpoints may be driven by the results of exploratory biomarker analyses from the initial dose escalation experiments.

The long-term safety and efficacy study is double blinded, randomized, and placebo controlled. There are two active study arms (A1PI-HC 100 mg or 200 mg aerosolized once daily) and a single placebo arm. Subjects are randomized in a 1:1:1 ratio, administered A1PI-HC or placebo for a total of six months, and then followed for an additional four-week safety-monitoring period. A total of 186 subjects are randomized, with the goal of obtaining evaluable data on 150 subjects. Subjects are monitored for safety as in the initial A1PI dose escalation study. Changes in the safety design aspects of the study may be required based on the results of the dose escalation experiments.

Confirmation of A1PI Efficacy and Safety in Diverse Populations

A third confirmatory study examines the long-term safety and efficacy of inhaled A1PI-HC maintenance therapy in CF subjects in diverse global populations. The parameters of this study depend on the results from the initial A1PI dose escalation and long term dosing experiments. The confirmatory study is currently planned as a double blind, randomized, placebo controlled study that uses one of the two doses of A1PI-HC from initial experiments (100 mg or 200 mg daily). Additional study parameters are summarized below:

Dose: The preferred dose of active agent is selected based on the results of the dose escalation and long term dosing studies. A single daily dose delivered by aerosol is delivered, and is compared to a matched placebo delivered in identical manner. The duration of dosing is one year, with a four-week safety follow-up period after the end of the dosing regimen.

Subjects: Subjects are recruited from approximately forty international sites, and are selected according to the inclusion and exclusion criteria utilized for the initial studies.

Endpoints: It is presently planned to use acute pulmonary exacerbation as the primary endpoint, utilizing criteria derived from the initial results. Secondary efficacy endpoint selection is also based on the initial results, and includes biomarkers and patient reported outcomes, and may additionally include economic outcomes.

Powering: This study is be powered for superiority, on the assumptions of a 20% reduction in mean exacerbation rate, and a placebo exacerbation rate of 1.5 per year. Powering will achieve an alpha of 0.05 and a beta of 0.20. This is estimated to require a total enrollment of 544 subjects, assuming a 20% dropout rate.

Dose Rationale

Wide ranges of doses of A1PI have been reported, including from 25 mg once daily to 350 mg twice daily. Although most studies of the effects of A1PI on exacerbations have reported improvement in one or more putative surrogate markers, none have used a validated clinical or laboratory endpoint. Griese et al., *Eur. Resp. J.* 29(2): 240-250 (2008); McElvaney et al. *Lancet* 337(8738): 392-394 (1991); Berger et al., *Pediatric Pulmonol.* 20: 421 (1995); Cantin et al., *Clin. Invest. Med.* 29(4): 201-207 (2006); Griese et al., *Electrophoresis* 22(1): 165-171 (2001); Kerem et al., *Am. J. Respir. Crit. Care. Med.* 179: A1185 (2009). Therefore, these studies do not permit selection of a dose based on the response of a generally accepted endpoint. Additionally, the variety of delivery devices and the evolution of aerosolization technology make it difficult to compare actual A1PI doses delivered to the lower respiratory tract across the studies.

A wide range of A1PI doses is well tolerated. Given this evidence of safety, and the inter-subject variability of inflammatory burden in CF patients, it is prudent to select at least one dose at the higher end of the range of previously studied doses. Reinhardt et al., *Eur. Respir. J.* 22: 497-502 (2003); Smountas et al., *Clin. Biochem.* 37: 1031-1036 (2004); Ordonez et al., *J. Pediatr.* 145: 689-692 (2004). This assures the greatest likelihood of reducing neutrophil elastase activity to a very low level across the intervention population. Normal subjects in the study by McElvaney et al. had undetectable neutrophil elastase activity in expectorated sputum. McElvaney et al. *Lancet* 337(8738): 392-394 (1991). Based on these results, 200 mg/day is chosen as the highest dose for these studies.

The selection of the lower dose to be tested is based on a recent study. Kerem et al utilized a dose of 80 mg A1PI per day, delivered by a nebulizer/compressor combination that showed favorable trends in putative surrogates. Kerem et al., *Am. J. Respir. Crit. Care. Med.* 179: A1185 (2009). Therefore, a dose of 100 mg per day, delivered by a nebulizer/compressor combination of equal or greater efficiency, is used as the low dose for these studies.

The duration of dosing in the A1PI dose escalation studies, 21 days, is based on the evaluation of A1PI-HC in $alpha_1$-antitrypsin deficiency. This provides multi-dose safety information prior to proceeding to longer durations of exposure. All subjects dosed with 100 mg for 21 days will have completed the study, and their data analyzed for safety, prior to initiating the 200 mg dose experiment.

Selection of the 12-Years and Up Age Range

These studies examine the efficacy of aerosolized A1PI-HC to delay the onset of or diminish the progression of pulmonary exacerbations. Accordingly, it is necessary and appropriate to select a population experiencing a significant number of exacerbations per year.

Figure 3:
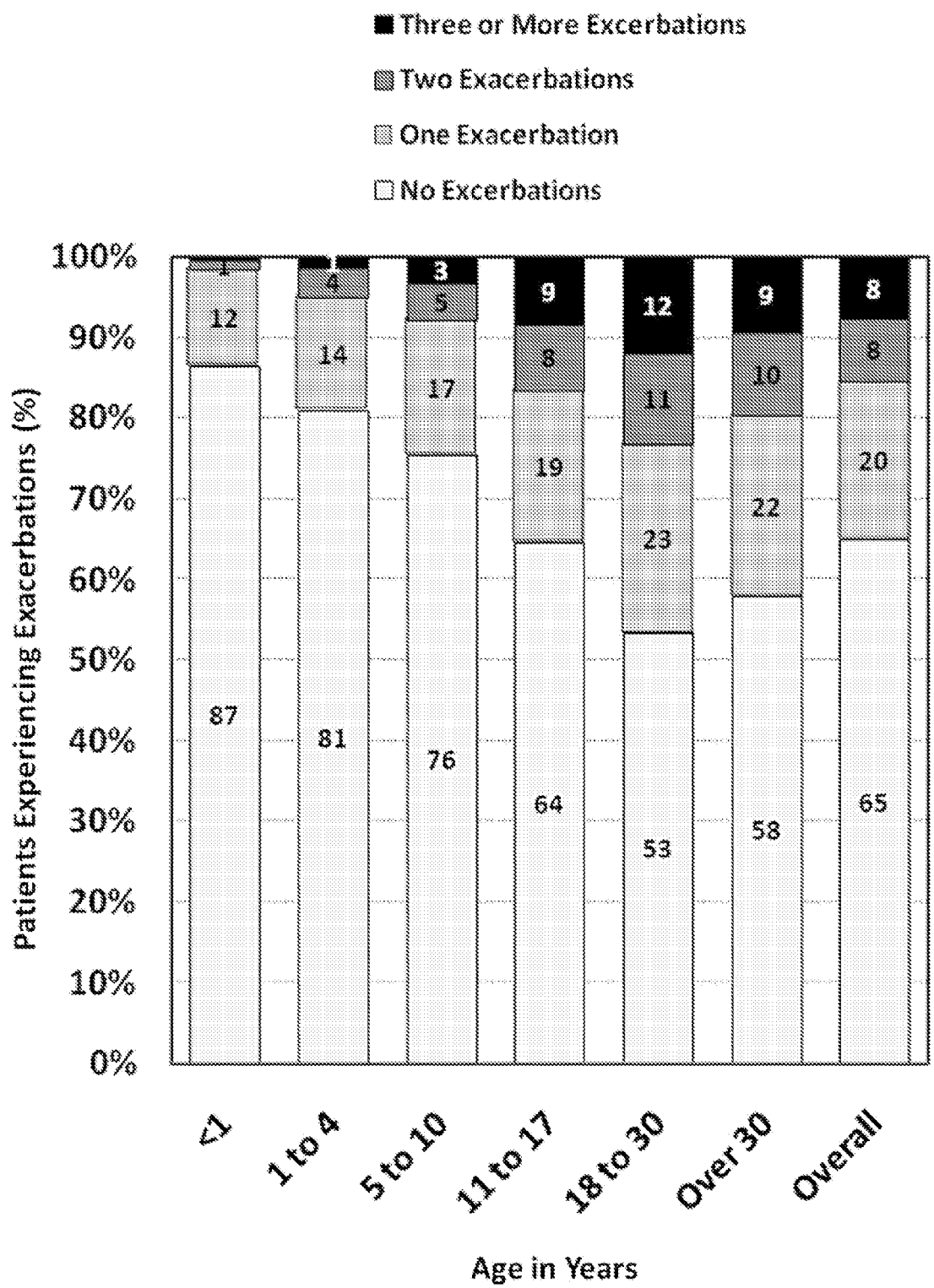
FIG. 3: Number of acute pulmonary exacerbations in CF patients in 2005 by age group. The x-axis breaks out the age ranges, with each age-range bar subdivided by the percentage of patients who have a certain number of exacerbations, as coded by color in the figure legend. Cystic Fibrosis Foundation Patient Registry Annual Data Report for 2005.

The CF Foundation estimates that 35% of cystic fibrosis patients have an acute pulmonary exacerbation annually. See FIG. 3; data from Cystic Fibrosis Foundation Patient Registry Annual Data Report for 2005. Cystic Fibrosis Foundation (2006); Cystic Fibrosis Foundation Patient Registry Annual Data Report to the Center Directors for 2008. Bethesda, Md.: Cystic Fibrosis Foundation (2009). Of these patients:

~70% have 1 exacerbation
~20% have 2 exacerbations
~10% have more than 2 exacerbations The number of exacerbations increases with age and disease severity, as shown in FIG. 3.

The target number of exacerbations in the placebo population is approximately two per year for the initial studies. Based on this target, CF patients 11 years of age and younger are excluded from the study, as few of these patients experience such an elevated rate of exacerbations. The age of 12 years is selected instead of 11 years to conform to the age cut off for adolescence generally used by the FDA.

Potentially applicable safety data for much of the adolescent age range are available from prior studies of aerosolized PROLASTIN® in CF subjects. These studies included 134 CF subjects that received doses ranging from a single 70 mg dose to 350 mg twice daily for 28 days. Of this population, 31 were adolescent subjects aged from 14 to 17 years.

Defining, Recording, and Reporting Exacerbations

All exacerbations are recorded in the medical chart and a case report form. Although exacerbations are part of the natural history of cystic fibrosis, exacerbations are considered adverse events in the study and reported accordingly. Exacerbations requiring hospitalization are recorded as significant adverse events (SAEs). Subjects are assessed for signs and symptoms of exacerbations at each study visit. They are contacted weekly by site personnel throughout the study to assess the presence or absence of exacerbation symptoms.

Despite the central role of acute pulmonary exacerbations in the progression of cystic fibrosis, no diagnostic indication has become widely accepted. The available diagnostic criteria and algorithms have focused on patient symptoms, physical examination, and laboratory data, and are primarily directed to facilitate treatment. Ramsey et al., *N. Engl. J. Med.* 340: 23-30 (1999); Rosenfeld et al., *J. Pediatr.* 139: 359-65 (2001); Goss and Burns, *Thorax* 62: 360-367 (2007). Reviews of studies incorporating these criteria have concluded that the signs and symptoms that were most predictive of a pulmonary exacerbation were: (i) an increased cough; (ii) a change in sputum (i.e., volume and/or consistency); (iii) decreased appetite and/or decreased weight; and (iv) a change in respiratory examination and/or respiratory rate. Dakin et al., *Pedi-* atr. Pulmonol. 31: 436-442 (2001); Rabin et al., Pediatr. Pulmonol. 37: 400-406 (2004). As used herein, an exacerbation is defined as a subject manifesting 4 out of 12 signs or symptoms according to Fuchs' criteria and requiring the use of an unscheduled course of a systemic or aerosolized antibiotic given at the discretion of the subject's physician. Fuchs et al., N. Engl. J. Med. 331(10): 637-42 (1994).

To meet Fuchs' criteria, four of the following twelve signs or symptoms must be present:
1. Change in sputum;
2. New or increased hemoptysis;
3. Increased cough;
4. Increased dyspnea;
5. Malaise, fatigue, or lethargy;
6. Temperature above 38° C.;
7. Anorexia or weight loss;
8. Sinus pain or tenderness;
9. Change in sinus discharge;
10. Change in physical examination of the chest;
11. Decrease in pulmonary function by 10 percent or more from a previously recorded value;
12. Radiographic changes indicative of pulmonary infection (subjects will require a chest radiograph during Visit 2 if not done within 6 months prior to randomization. The chest radiograph must be retrievable).

See Fuchs et al., N. Engl. J. Med. 331(10): 637-42 (1994).

In addition, clinical signs and/or symptoms determined by the Investigator to constitute an exacerbation are collected and analyzed separately.

Exacerbation severity is assessed based on the Investigator's judgment. Exacerbation severity is analyzed according to Investigator-rated severity as well as pre-defined severity criteria as follows:

Mild Exacerbation: involves an increase in one or more respiratory symptoms (dyspnea, cough, and/or sputum) that is controlled by the subject with an increase in the usual medication;

Moderate Exacerbation: requires outpatient antibiotics;

Severe Exacerbation: describes exacerbations that require hospitalization (an emergency department stay>24 hours is considered a hospitalization). If a subject is hospitalized for an exacerbation, it is reported as an SAE.

The start and stop dates of an exacerbation are recorded in the CRF.

If a subject is hospitalized for an exacerbation, the standard of care should be followed. The following tests are recommended (copies of test results should be included if performed):

Clinical Assessment (including vital signs);
Post bronchodilator PFTs (spirometry);
Quantification of diffusion capacity;
Arterial blood gases (ABG);
Complete Blood Count (CBC) with differential and red blood cell morphology;
Chest X-rays (posterior-anterior and lateral);
High-sensitivity C-reactive protein test (i.e., hs-CRP; serum sample);
Sputum color/bacteriology; and
Serum sample to be drawn and stored for later analysis.

Any subject experiencing a severe exacerbation at any time after randomization is discontinued from the study drug. The subject will continue to be monitored via weekly telephone calls and is requested to return for an Early Discontinuation/Follow-up visit.

Selection of Biomarkers

During the course of the initial studies, data are collected for a number of biomarkers in order to assess dose adequacy in regard to neutralization of the subjects' NE burden; to elucidate potential predictors of clinical response that may guide future studies and clinician treatment decisions; and to obtain a better understanding of potential additional mechanisms of action of A1PI-HC in the management of cystic fibrosis. Biomarker data is collected from both sputum and blood samples, as indicated below.

Biomarkers in Sputum:
amount of total A1PI
NE activity;
semi-quantitative bacterial cultures;
leukotriene B4 (LTB4); and
additional biomarkers as clinically determined.

Measurement of A1PI in sputum permits evaluation of delivery the aerosolized study drug. Although native A1PI is present, it is expected that total A1PI will rise as compared to pre-study levels in the active experimental arms. Additionally, sputum NE activity allows evaluation of the degree to which A1PI has successfully inhibited NE's ability to destroy elastin.

Semi-quantitative bacterial cultures of sputa are obtained. P. aeruginosa colony counts correlate with response to therapy in CF respiratory exacerbation, and aerosol delivered A1PI-HC reduces P. aeruginosa colony counts. Cazzola et al., Eur. Respir. J. 31(2): 416-68 (2008); Griese et al., Eur. Resp. J. 29(2): 240-250 (2008).

Other biomarkers in sputum are measured as possible given the limited volume of sputum. The assays of primary interest include the pro-inflammatory cytokines TNF-α, IL-6 and IL-8. Previous studies of aerosolized A1PI-HC in CF have reductions in these mediators. Griese et al., Eur. Resp. J. 29(2): 240-250 (2008); Cantin et al., Clin. Invest. Med. 29(4): 201-207 (2006). Blood levels of cytokines are evaluated to explore a potential correlation with sputum levels.

Biomarkers in Blood:
TNF-α
IL-6, 8, 10

Biomarkers in Urine:
Desmosine, isodesmosine

Biomarkers in sputum, blood, and urine are selected based on their association with inhibition of neutrophil elastase (NE) and the resulting degradation of mature elastin, or their association with the pro-inflammatory state within the lungs.

Finally, desmosine and isodesmosine urine levels are evaluated. These molecules are breakdown products of mature elastin, the primary target of NE, and have been demonstrated to be elevated in several tissues during destructive pulmonary diseases.

What is claimed is:

1. A method of diminishing progression of one or more of a first set of symptoms associated with pulmonary exacerbations from worsening and/or increasing in severity in a subject in need thereof comprising:
   identifying the subject as in need of diminishing progression of said one or more of the first set of symptoms associated with pulmonary exacerbations from worsening and/or increasing in severity by identifying one or more of a second set of symptoms predictive of the pulmonary exacerbations, wherein the second set of symptoms comprises:
   i) an increased cough
   ii) a change in sputum
   iii) decreased appetite and/or decreased weight;
   iv) a change in respiratory examination and/or respiratory rate; and
   administering to the identified subject an effective amount of Alpha$_1$-proteinase inhibitor (A1PI) via inhalation prior to onset of said one or more of the first set of symptoms, wherein the first set of symptoms comprises:
   (a) shortness of breath;
   (b) fatigue;
   (c) a chronic cough;
   (d) a reduction in forced expiratory volume (FEV$_1$); and
   (e) decline in expiratory gas markers of respiratory inflammation;
   wherein the administration is carried out at least daily for a plurality of months.

2. The method of claim 1, wherein the A1PI is aerosolized.

3. The method of claim 1, wherein the A1PI is administered using a nebulizer.

4. The method of claim 1, wherein the effective amount of A1PI is about 25 mg to about 750 mg A1PI per day.

5. The method of claim 1, wherein the effective amount of A1PI is about 0.5 mg/kg/day to about 15 mg/kg/day.

6. The method of claim 1, wherein the subject in need thereof is at least 12 years old.

7. The method of claim 1, wherein the pulmonary exacerbations are associated with cystic fibrosis, chronic obstructive pulmonary disease (COPD), alpha$_1$-antitrypsin deficiency (AATD), emphysema, asthma, mycobacterial infection, pneumonia, bronchiectasis, or chronic bronchitis.

8. The method of claim 1, wherein the pulmonary exacerbations are associated with increased severity of exacerbations; increased frequency of exacerbations; decreased lung function; decreased FEV1; increased pulmonary tissue loss; decreased A1PI levels; increased pulmonary elastase levels; increased pulmonary infections; increased pulmonary bacterial load; or increased cardiac dysrhythmia.

9. The method of claim 1, wherein the A1PI is recombinant A1PI.

10. The method of claim 1, wherein the A1PI is purified by a method for purifying A1PI from an aqueous solution containing A1PI, the method comprising:
    removing a portion of contaminating proteins from the aqueous solution by precipitation in order to obtain a purified solution containing A1PI;
    passing the purified solution through an anion exchange resin so that A1PI binds to the anion exchange resin;
    eluting A1PI from the anion exchange resin to obtain an eluted solution containing A1PI;
    passing the eluted solution through a cation exchange resin; and
    collecting a flow-through from the cation exchange resin that contains A1PI.

11. The method of claim 10, further comprising:
    contacting the eluted solution or the flow-through with a hydrophobic adsorbent of at least one HIC medium.

12. A method according to claim 1;
    wherein the A1PI is aerosolized;
    wherein the A1PI is administered using a nebulizer;
    wherein the effective amount of A1PI is about 25 mg to about 750 mg A1PI per day;

wherein the effective amount of A1PI is about 0.5 mg/kg/day to about 15 mg/kg/day;
wherein the subject is at least 12 years old.

13. The method according to claim 1 further comprising:
identifying the subject who was identified as in need of diminishing progression of the one or more of the first set of symptoms associated with pulmonary exacerbations from worsening and/or increasing in severity as having elevated risk for pulmonary exacerbations by evaluating one or more of the subject's
(a) age;
(b) history of exacerbations;
(c) lung function ($FEV_1$);
(d) chronic productive cough (mucus producing)
(e) upper and lower airways' infectious pathogen burden;
(f) expiratory gas markers of respiratory inflammation;
(g) response to exogenous challenge testing for airways hyperresponsiveness;
(h) number and classes of concomitant medications;
(i) genetic risk profile for respiratory disease; and
(j) environmental risk factors selected from the group consisting of smoking history, allergies, occupational exposure to pulmonary irritants, and/or exposure to air pollution.

14. The method according to claim 1, wherein the subject has one or more of
(a) an elevated risk for acute pulmonary exacerbation;
(b) a significant decline of respiratory function; or
(c) a history of pulmonary exacerbations associated with cystic fibrosis, chronic obstructive pulmonary disease (COPD), $alpha_1$-antitrypsin deficiency (AATD), emphysema, asthma, mycobacterial infection, pneumonia, bronchiectasis, or chronic bronchitis;
wherein the subject receives inhaled A1PI administered via aerosol generated by a nebulizer one or more times per day; and
wherein the cumulative effective dose of A1PI is from about 25 mg to about 750 mg per day.

15. The method according to claim 1, wherein the method results in:
reduced hospitalization;
reduced intensive care or mechanical ventilation need;
reduced healthcare utilization or burden;
reduced absences from school or work;
decreased antibiotic need;
decreased steroid need;
decreased relapse frequency; and
decreased morbidity.

* * * * *

SEQUENCE LISTING

<160> NUMBER OF SEQ ID NOS: 1

<210> SEQ ID NO 1
<211> LENGTH: 418
<212> TYPE: PRT

```
<213> ORGANISM: Homo sapiens
<220> FEATURE:
<221> NAME/KEY: SIGNAL
<222> LOCATION: (1)..(24)
<220> FEATURE:
<221> NAME/KEY: mat_peptide
<222> LOCATION: (25)..(418)
<220> FEATURE:
<221> NAME/KEY: CARBOHYD
<222> LOCATION: (70)..(70)
<220> FEATURE:
<221> NAME/KEY: CARBOHYD
<222> LOCATION: (107)..(107)
<220> FEATURE:
<221> NAME/KEY: MISC_FEATURE
<222> LOCATION: (256)..(256)
<223> OTHER INFORMATION: C256 S-nitrosylation
<220> FEATURE:
<221> NAME/KEY: CARBOHYD
<222> LOCATION: (271)..(271)
<220> FEATURE:
<221> NAME/KEY: MISC_FEATURE
<222> LOCATION: (376)..(376)
<223> OTHER INFORMATION: proteolytic cleavage site
<220> FEATURE:
<221> NAME/KEY: MISC_FEATURE
<222> LOCATION: (382)..(383)
<223> OTHER INFORMATION: reactive bond

<400> SEQUENCE: 1

Met Pro Ser Ser Val Ser Trp Gly Ile Leu Leu Leu Ala Gly Leu Cys
            -20                 -15                 -10

Cys Leu Val Pro Val Ser Leu Ala Glu Asp Pro Gln Gly Asp Ala Ala
         -5                  -1  1               5

Gln Lys Thr Asp Thr Ser His His Asp Gln Asp His Pro Thr Phe Asn
         10                  15                  20

Lys Ile Thr Pro Asn Leu Ala Glu Phe Ala Phe Ser Leu Tyr Arg Gln
 25                  30                  35                  40

Leu Ala His Gln Ser Asn Ser Thr Asn Ile Phe Phe Ser Pro Val Ser
                 45                  50                  55

Ile Ala Thr Ala Phe Ala Met Leu Ser Leu Gly Thr Lys Ala Asp Thr
                 60                  65                  70

His Asp Glu Ile Leu Glu Gly Leu Asn Phe Asn Leu Thr Glu Ile Pro
             75                  80                  85

Glu Ala Gln Ile His Glu Gly Phe Gln Glu Leu Leu Arg Thr Leu Asn
         90                  95                 100

Gln Pro Asp Ser Gln Leu Gln Leu Thr Thr Gly Asn Gly Leu Phe Leu
105                 110                 115                 120

Ser Glu Gly Leu Lys Leu Val Asp Lys Phe Leu Glu Asp Val Lys Lys
                125                 130                 135

Leu Tyr His Ser Glu Ala Phe Thr Val Asn Phe Gly Asp Thr Glu Glu
                140                 145                 150

Ala Lys Lys Gln Ile Asn Asp Tyr Val Glu Lys Gly Thr Gln Gly Lys
                155                 160                 165

Ile Val Asp Leu Val Lys Glu Leu Asp Arg Asp Thr Val Phe Ala Leu
            170                 175                 180

Val Asn Tyr Ile Phe Phe Lys Gly Lys Trp Glu Arg Pro Phe Glu Val
185                 190                 195                 200

Lys Asp Thr Glu Glu Glu Asp Phe His Val Asp Gln Val Thr Thr Val
                205                 210                 215

Lys Val Pro Met Met Lys Arg Leu Gly Met Phe Asn Ile Gln His Cys
                220                 225                 230
```

```
Lys Lys Leu Ser Ser Trp Val Leu Leu Met Lys Tyr Leu Gly Asn Ala
        235             240             245

Thr Ala Ile Phe Phe Leu Pro Asp Glu Gly Lys Leu Gln His Leu Glu
    250             255             260

Asn Glu Leu Thr His Asp Ile Ile Thr Lys Phe Leu Glu Asn Glu Asp
265             270             275             280

Arg Arg Ser Ala Ser Leu His Leu Pro Lys Leu Ser Ile Thr Gly Thr
            285             290             295

Tyr Asp Leu Lys Ser Val Leu Gly Gln Leu Gly Ile Thr Lys Val Phe
        300             305             310

Ser Asn Gly Ala Asp Leu Ser Gly Val Thr Glu Glu Ala Pro Leu Lys
        315             320             325

Leu Ser Lys Ala Val His Lys Ala Val Leu Thr Ile Asp Glu Lys Gly
        330             335             340

Thr Glu Ala Ala Gly Ala Met Phe Leu Glu Ala Ile Pro Met Ser Ile
345             350             355             360

Pro Pro Glu Val Lys Phe Asn Lys Pro Phe Val Phe Leu Met Ile Glu
            365             370             375

Gln Asn Thr Lys Ser Pro Leu Phe Met Gly Lys Val Val Asn Pro Thr
            380             385             390

Gln Lys
```